United States Patent [19]

Ko et al.

[11] Patent Number: 6,011,198
[45] Date of Patent: Jan. 4, 2000

[54] CONSTRUCTS AND METHODS FOR ENHANCING PROTEIN LEVELS IN PHOTOSYNTHETIC ORGANISMS

[75] Inventors: Kenton Ko; Zdenka W. Ko, both of Kingston, Canada; Carlos A. Labate, Piracicaba, Brazil; Antonio Granell, Alginet, Spain

[73] Assignee: Queen's University at Kingston, Kingston, Canada

[21] Appl. No.: 08/759,463

[22] Filed: Dec. 5, 1996

Related U.S. Application Data

[63] Continuation-in-part of application No. 08/568,168, Dec. 6, 1995.

[51] Int. Cl.[7] .......................... C12N 15/09; C12N 15/29; C12N 15/82; A01H 4/00
[52] U.S. Cl. ..................... 800/205; 435/69.1; 435/172.3; 435/320.1; 435/419; 435/69.7; 435/69.8; 536/23.4; 536/24.1; 536/23.6
[58] Field of Search ................................ 435/69.1, 172.3, 435/320.1, 419, 69.7, 69.8; 536/23.4, 24.1, 23.6; 800/205

[56] References Cited

U.S. PATENT DOCUMENTS

| | | | |
|---|---|---|---|
| 5,656,496 | 8/1997 | Quail et al. | 435/320.1 |
| 5,717,084 | 2/1998 | Herrera-Estrella et al. | 536/23.4 |
| 5,728,925 | 3/1998 | Herrera-Estrella et al. | 800/205 |

FOREIGN PATENT DOCUMENTS

| | | |
|---|---|---|
| 0189707B1 | 8/1993 | European Pat. Off. . |
| 90/02189 | 3/1990 | WIPO . |

OTHER PUBLICATIONS

Barzda, V., Istokovics, A., Simidjiev, I., and Garab, G., "Structural flexibility of chiral macroaggregates of light–harvesting chlorophyll a/b pigment–protein complexes. Light–induced reversible structural changes associated with energy dissipation", *Biochem.* 35:8981–8985 (1996).

Chory, J., Chatterjee, M., Cook, R.K., Elich, T., Fankhauser, C., Li, J., Nagpai, P., Neff, M., Pepper, A., Poole, D., Reed, J., and Vitart, V., "From seed germination to flowering, light controls plant development via the pigment phytochrome", *Proc. Natl. Acad. Sci. USA* 93: 12066–12071 (1996).

Eskins, K., Warner, K., and Felker, F.C., "Light quality during early seedling development influences the morphology and bitter taste intensity of mature lettuce (*Lactuca sativa*) leaves", *J. Plant Physiol.* 147: 709–713 (1996).

Flachman, R., and Kühlbrandt, W., "Crystallization and identification of an assembly defect of recombinant antenna complexes produced in transgenic tobacco plants", *Proc. Natl. Acad. Sci. USA* 93: 14966–14971 (1996).

Galbraith, D.W., "Flow cytometric analysis of plant genomes", *Meth. Cell Biol.* 33: 549–562 (1990).

Hofmann, E., Wrench, P.M., Sharples, F.P., Hiller, R.G., Welte, W., Diederichs, K., "Structural basis of light harvesting by carotenoids: peridinin–chlorophyll–protein from *Amphidinium carterae*", *Science* 272:1788–1791 (1996).

Kozaki, A., and Takeba, G., "Photorespiration protects C3 plants from photooxidation", *Nature* 384:557–560 (1996).

Lee, J.W., Tevault, C.V., Owens, T.G., and Greenbaum, E., "Oxygenic photoautotrophic growth without photosystem I", *Science* 273: 364–367 (1996).

Meehan, L., Harkins, K., Chory, J., and Rodermel, S., "Lhcb transcription is coordinated with cell size and chlorophyll accumulation. Studies on fluorescence–activated, cell–sorter–purified single cells from wild–type and immutans *Arabidopsis thaliana*", *Plant Physiol.* 112: 953–963 (1996).

Moffat, A.S., "Form follows function when plants harvest light", *Science* 272: 1743–1744 (1996).

Morcuende, R., Pérez, P., Martínez–Carrasco, R., Del Molino, I.M., and Sánchez De La Puente, L., "Long–and short–term responses of leaf carbohydrate levels and photosynthesis to decreased sink demand in soybean", *Plant. Cell and Environ.* 19: 976–982 (1996).

Quail, P.H., "A new vision for plant productivity", *Nature Biotech.* 14: 945 (1996).

Robson, P.R.H., McCormac, A.C., Irvine, A.S., and Smith, H., "Genetic engineering of harvest index in tobacco through overexpression of a phytochrome gene", *Nature Biotech.* 14: 995–998 (1996).

Ko et al. Research in Photosynthesis vol. III: Proceedings of the IX International Congress on Photosynthesis, Kluwer Academic Press, pp. 445–448, 1992.

Aoyagi et al. The pea rbcS–3A enhancer–like element directs cell–specific expression in transgenic tobacco. Mol. Gen. Genet. (1988) 213: 179–185.

Anderson et al. Synthesis of the small subunit of ribulose bisphosphate carboxylase from genes coned into plasmids containing the SP6 promoter. Biochem. J. (1986) 240, 709–715.

Broido S, Loyter A, Vainstein A. Transient expression of photosynthetic genes in transfected albinoid petunia protoplasts and correct processing of newly synthesized chloroplast–destined polypeptides. Physiologia Plantarum. 88:259–266, 1993.

Cheung AY, Bogorad L, Van Montagu M, Schell J. Relocating a gene for herbicide tolerance: A chloroplast gene is converted into a nuclear gene. Proc Natl Acad Sci USA. 85:391–395, Jan. 1988.

*Primary Examiner*—Douglas W. Robinson
*Assistant Examiner*—Thomas Haas
*Attorney, Agent, or Firm*—Hamilton, Brook, Smith & Reynolds, P.C.

[57] ABSTRACT

This invention provides novel gene constructs which enhance the efficiency of plant cells and cells of other photosynthetic organisms. Also provided are transgenic plants and seeds which overexpress proteins. Methods to elevate the amount of plastid proteins in plants and photosynthetic organisms are exemplified.

40 Claims, 16 Drawing Sheets

```
        TCCATGAACGGATTCTAGAATTGCAAAGAAAATCTCCAACTAGCCATAGCTTTAGATAAC   -56

ACACGATAAGAGCATCTGCATTATAAATACAGACTCATATTCATCTTACAAAATCACCAT     5

TGATAAGGATACAATTATCAAAAGCATAACAATCTTTTCAATTTCATTGCAATATAATAC    65

MetAlaAlaSerSerSerSerSerMetAlaLeuSerSerProThrLeuAlaGlyLys
           ACGATGGCCGCATCATCATCATCATCCATGGCTCTCTCTTCTCCAACCTTGGCTGGCAAG   125
                                                              5'/NH₂
                                                                ↓
    20     GlnLeuLysLeuAsnProSerSerGlnGluLeuGlyAlaAlaArgPheThrMetArgLys
           CAACTCAAGCTGAACCCATCAAGCCAAGAATTGGGAGCTGCAAGGTTCACCATGAGGAAG   185

40     SerAlaThrThrLysLysValAlaSerSerGlySerProTrpTyrGlyProAspArgVal
           TCTGCTACCACCAAGAAAGTAGCTTCCTCTGGAAGCCCATGGTACGGACCAGACCGTGTT   245
             C              C         A T            C      C
             *                        Ser            His

60     LysTyrLeuGlyProPheSerGlyGluSerProSerTyrLeuThrGlyGluPheProGly
           AAGTACTTAGGCCCATTCTCCGGTGAGTCTCCATCCTACTTGACTGGAGAGTTCCCCGGT   305
                C                        A         C              A

80     AspTyrGlyTrpAspThrAlaGlyLeuSerAlaAspProGlnThrPheSerLysAsnArg
           GACTACGGTTGGGACACTGCCGGACTCTCTGCTGACCCACAGACATTCTCCAAGAACCGT   365
                       T    T      C  T                TG
                                                       Ala

100     GluLeuGluValIleHisSerArgTrpAlaMetLeuGlyAlaLeuGlyCysValPhePro
           GAGCTTGAAGTCATCCACTCCAGATGGGCTATGTTGGGTGCTTTGGGATGTGTCTTCCCA   425
                    T                              A  C

120     GluLeuLeuSerArgAsnGlyValLysPheGlyGluAlaValTrpPheLysAlaGlySer
           GAGCTTTTGTCTCGCAACGGTGTTAAATTCGGCGAAGCTGTGTGGTTCAAGGCAGGATCT   485
                                    T                A

140     GlnIlePheSerGluGlyGlyLeuAspTyrLeuGlyAsnProSerLeuValHisAlaGln
           CAAATCTTTAGTGAGGGTGGACTTGATTACTTGGGCAACCCAAGCTTGGTCCATGCTCAA   545
                           C              C
```

FIGURE 1A

```
160  SerIleLeuAlaIleTrpAlaThrGlnValIleLeuMetGlyAlaValGluGlyTyrArg
     AGCATCCTTGCCATATGGGCCACTCAGGTTATCTTGATGGGAGCTGTCGAAGGTTACCGT    605
                  C                                T

180  IleAlaGlyGlyProLeuGlyGluValValAspProLeuTyrProGlyGlySerPheAsp
     ATTGCCGGTGGGCCTCTCGGTGAGGTGGTTGATCCACTTTACCCAGGTGGAAGCTTTGAT    665
            C   T        T   C          T T    T

200  ProLeuGlyLeuAlaAspAspProGluAlaPheAlaGluLeuLysValLysGluLeuLys
     CCATTGGGCTTAGCTGATGATCCAGAAGCATTCGCAGAATTGAAGGTGAAGGAACTCAAG    725
        A         A TA          T T       A       A        G
                       GluVal

220  AsnGlyArgLeuAlaMetPheSerMetPheGlyPhePheValGlnAlaIleValThrGly
     AACGGTAGATTAGCCATGTTCTCAATGTTTGGATTCTTCGTTCAAGCTATTGTAACTGGA    785
                         T      T   T

240  LysGlyProLeuGluAsnLeuAlaAspHisLeuAlaAspProValAsnAsnAsnAlaTrp
     AAGGGTCCTTTGGAGAACCTTGCTGATCATCTTGCAGACCCAGTCAACAACAATGCATGG    845
                  C                C        G        C

260  SerTyrAlaThrAsnPheValProGlyLys
     TCATATGCCACCAACTTTGTTCCCGGAAAATAAACACTCTTATATTTAT-----------    894
          T                 G G     A       G        GTTATTGGTGA

---ATGTTTTTGTGATAGTAATCTTCTTCCCAATTCAATGTGAATTATTATCATTATCAT    951
     AGT    A    T        G     -    T        G   GG             --

TATCATGTGGGTATGCATAGGTTCACTAATACAAGATGATGGATGCTTTTTTTTTACCAA    1011
     ----G    T       G   A        TG AC     TCG---         T*

3'/COOH
          ↓
     ATTTTAAATTTTATGTTTCATGCTTTCCATTGCTAGACAT
```

FIGURE 1B

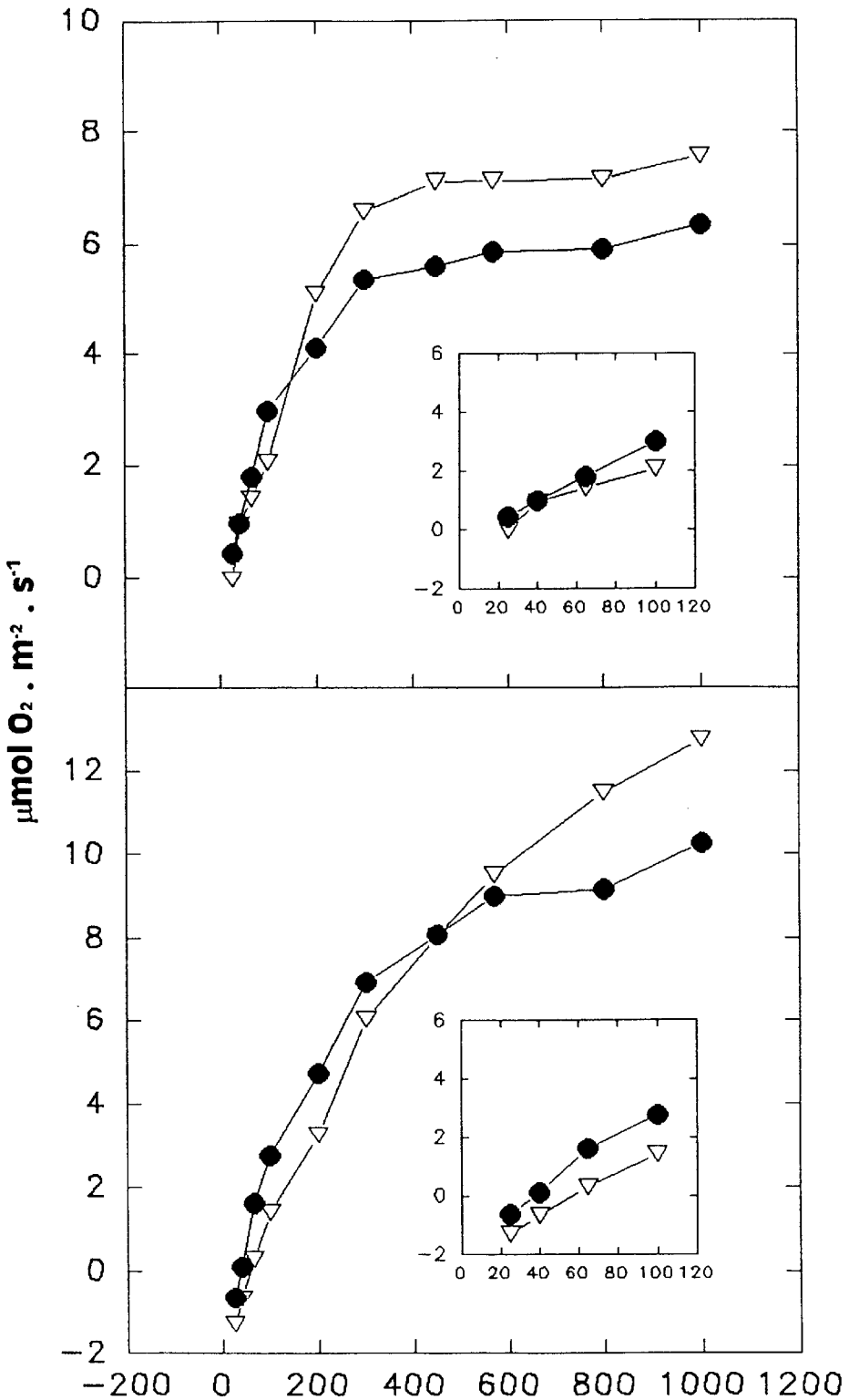

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 1166 base pairs
      (B) TYPE: nucleic acid
      (C) STRANDEDNESS: double
      (D) TOPOLOGY: linear (ix) FEATURE:
      (A) NAME/KEY: CDS
      (B) LOCATION:184..990

(xi) SEQUENCE DESCRIPTION: SEQ ID NO: 1:

```
TCCATGAACG GATTCTAGAA TTGCAAAGAA AATCTCCAAC TAGCCATAGC TTTAGATAAC      60

ACACGATAAG AGCATCTGCA TTATAAATAC AGACTCATAT TCATCTTACA AAATCACCAT     120
```

```
TGATAAGGAT ACAATTATCA AAAGCATAAC AATCTTTTCA ATTTCATTGC AATATAATAC       180

ACG ATG GCC GCA TCA TCA TCA TCA TCC ATG GCT CTC TCT TCT CCA ACC       228
    Met Ala Ala Ser Ser Ser Ser Ser Met Ala Leu Ser Ser Pro Thr
    1               5                   10                  15

TTG GCT GGC AAG CAA CTC AAG CTG AAC CCA TCA AGC CAA GAA TTG GGA       276
Leu Ala Gly Lys Gln Leu Lys Leu Asn Pro Ser Ser Gln Glu Leu Gly
                20                  25                  30

GCT GCA AGG TTC ACC ATG AGG AAG TCT GCT ACC ACC AAG AAA GTA GCT       324
Ala Ala Arg Phe Thr Met Arg Lys Ser Ala Thr Thr Lys Lys Val Ala
            35                  40                  45

TCC TCT GGA AGC CCA TGG TAC GGA CCA GAC CGT GTT AAG TAC TTA GGC       372
Ser Ser Gly Ser Pro Trp Tyr Gly Pro Asp Arg Val Lys Tyr Leu Gly
        50                  55                  60

CCA TTC TCC GGT GAG TCT CCA TCC TAC TTG ACT GGA GAG TTC CCC GGT       420
Pro Phe Ser Gly Glu Ser Pro Ser Tyr Leu Thr Gly Glu Phe Pro Gly
    65                  70                  75

GAC TAC GGT TGG GAC ACT GCC GGA CTC TCT GCT GAC CCA CAG ACA TTC       468
Asp Tyr Gly Trp Asp Thr Ala Gly Leu Ser Ala Asp Pro Gln Thr Phe
80                  85                  90                  95

TCC AAG AAC CGT GAG CTT GAA GTC ATC CAC TCC AGA TGG GCT ATG TTG       516
Ser Lys Asn Arg Glu Leu Glu Val Ile His Ser Arg Trp Ala Met Leu
                100                 105                 110

GGT GCT TTG GGA TGT GTC TTC CCA GAG CTT TTG TCT CGC AAC GGT GTT       564
Gly Ala Leu Gly Cys Val Phe Pro Glu Leu Leu Ser Arg Asn Gly Val
            115                 120                 125

AAA TTC GGC GAA GCT GTG TGG TTC AAG GCA GGA TCT CAA ATC TTT AGT       612
Lys Phe Gly Glu Ala Val Trp Phe Lys Ala Gly Ser Gln Ile Phe Ser
        130                 135                 140

GAG GGT GGA CTT GAT TAC TTG GGC AAC CCA AGC TTG GTC CAT GCT CAA       660
Glu Gly Gly Leu Asp Tyr Leu Gly Asn Pro Ser Leu Val His Ala Gln
    145                 150                 155

AGC ATC CTT GCC ATA TGG GCC ACT CAG GTT ATC TTG ATG GGA GCT GTC       708
Ser Ile Leu Ala Ile Trp Ala Thr Gln Val Ile Leu Met Gly Ala Val
160                 165                 170                 175

GAA GGT TAC CGT ATT GCC GGT GGG CCT CTC GGT GAG GTG GTT GAT CCA       756
Glu Gly Tyr Arg Ile Ala Gly Gly Pro Leu Gly Glu Val Val Asp Pro
                180                 185                 190

CTT TAC CCA GGT GGA AGC TTT GAT CCA TTG GGC TTA GCT GAT GAT CCA       804
Leu Tyr Pro Gly Gly Ser Phe Asp Pro Leu Gly Leu Ala Asp Asp Pro
            195                 200                 205

GAA GCA TTC GCA GAA TTG AAG GTG AAG GAA CTC AAG AAC GGT AGA TTA       852
Glu Ala Phe Ala Glu Leu Lys Val Lys Glu Leu Lys Asn Gly Arg Leu
        210                 215                 220

GCC ATG TTC TCA ATG TTT GGA TTC TTC GTT CAA GCT ATT GTA ACT GGA       900
Ala Met Phe Ser Met Phe Gly Phe Phe Val Gln Ala Ile Val Thr Gly
    225                 230                 235

AAG GGT CCT TTG GAG AAC CTT GCT GAT CAT CTT GCA GAC CCA GTC AAC       948
Lys Gly Pro Leu Glu Asn Leu Ala Asp His Leu Ala Asp Pro Val Asn
240                 245                 250                 255

AAC AAT GCA TGG TCA TAT GCC ACC AAC TTT GTT CCC GGA AAA              990
Asn Asn Ala Trp Ser Tyr Ala Thr Asn Phe Val Pro Gly Lys
                260                 265

TAAACACTCT TATATTTATA TGTTTTTGTG ATAGTAATCT TCTTCCCAAT TCAATGTGAA     1050

TTATTATCAT TATCATTATC ATGTGGGTAT GCATAGGTTC ACTAATACAA GATGATGGAT    1110

GCTTTTTTTT TACCAAATTT TAAATTTTAT GTTTCATGCT TTCCATTGCT AGACAT        1166
```

(2) INFORMATION FOR SEQ ID NO: 2:

(i) SEQUENCE CHARACTERISTICS:
        (A) LENGTH: 269 amino acids
        (B) TYPE: amino acid
        (D) TOPOLOGY: linear (ii) MOLECULE TYPE: protein (xi) SEQUENCE DESCRIPTION: SEQ ID NO: 2:

Met Ala Ala Ser Ser Ser Ser Met Ala Leu Ser Ser Pro Thr Leu
 1               5                  10                  15

Ala Gly Lys Gln Leu Lys Leu Asn Pro Ser Ser Gln Glu Leu Gly Ala
            20                  25                  30

Ala Arg Phe Thr Met Arg Lys Ser Ala Thr Thr Lys Lys Val Ala Ser
        35                  40                  45

Ser Gly Ser Pro Trp Tyr Gly Pro Asp Arg Val Lys Tyr Leu Gly Pro
    50                  55                  60

Phe Ser Gly Glu Ser Pro Ser Tyr Leu Thr Gly Glu Phe Pro Gly Asp
65                  70                  75                  80

Tyr Gly Trp Asp Thr Ala Gly Leu Ser Ala Asp Pro Gln Thr Phe Ser
                85                  90                  95

Lys Asn Arg Glu Leu Glu Val Ile His Ser Arg Trp Ala Met Leu Gly
            100                 105                 110

Ala Leu Gly Cys Val Phe Pro Glu Leu Leu Ser Arg Asn Gly Val Lys
        115                 120                 125

Phe Gly Glu Ala Val Trp Phe Lys Ala Gly Ser Gln Ile Phe Ser Glu
    130                 135                 140

Gly Gly Leu Asp Tyr Leu Gly Asn Pro Ser Leu Val His Ala Gln Ser
145                 150                 155                 160

Ile Leu Ala Ile Trp Ala Thr Gln Val Ile Leu Met Gly Ala Val Glu
                165                 170                 175

Gly Tyr Arg Ile Ala Gly Gly Pro Leu Gly Glu Val Val Asp Pro Leu
            180                 185                 190

Tyr Pro Gly Gly Ser Phe Asp Pro Leu Gly Leu Ala Asp Asp Pro Glu
        195                 200                 205

Ala Phe Ala Glu Leu Lys Val Lys Glu Leu Lys Asn Gly Arg Leu Ala
    210                 215                 220

Met Phe Ser Met Phe Gly Phe Val Gln Ala Ile Val Thr Gly Lys
225                 230                 235                 240

Gly Pro Leu Glu Asn Leu Ala Asp His Leu Ala Asp Pro Val Asn Asn
                245                 250                 255

Asn Ala Trp Ser Tyr Ala Thr Asn Phe Val Pro Gly Lys
            260                 265

(2) INFORMATION FOR SEQ ID NO: 3:

(i) SEQUENCE CHARACTERISTICS:
        (A) LENGTH: 221 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION:30..221

(xi) SEQUENCE DESCRIPTION: SEQ ID NO: 3:

ACGTTGCAAT TCATACAGAA GTGAGAAAA ATG GCT TCT ATG ATA TCC TCT TCC     53
                                Met Ala Ser Met Ile Ser Ser Ser
                                270                 275

```
GCT GTG ACA ACA GTC AGC CGT GCC TCT AGG GGG CAA TCC GCC GCA GTG        101
Ala Val Thr Thr Val Ser Arg Ala Ser Arg Gly Gln Ser Ala Ala Val
        280                 285                 290

GCT CCA TTC GGC GGC CTC AAA TCC ATG ACT GGA TTC CCA GTG AAG AAG        149
Ala Pro Phe Gly Gly Leu Lys Ser Met Thr Gly Phe Pro Val Lys Lys
    295                 300                 305

GTC AAC ACT GAC ATT ACT TCC ATT ACA AGC AAT GGT GGA AGA GTA AAG        197
Val Asn Thr Asp Ile Thr Ser Ile Thr Ser Asn Gly Gly Arg Val Lys
310                 315                 320                 325

TGC ATG GAT CCT GTA GAG AAG TCT                                        221
Cys Met Asp Pro Val Glu Lys Ser
                330

(2) INFORMATION FOR SEQ ID NO: 4:

(i) SEQUENCE CHARACTERISTICS:
        (A) LENGTH: 64 amino acids
        (B) TYPE: amino acid
        (D) TOPOLOGY: linear (ii) MOLECULE TYPE: protein (xi) SEQUENCE DESCRIPTION: SEQ ID NO: 4:

Met Ala Ser Met Ile Ser Ser Ser Ala Val Thr Thr Val Ser Arg Ala
1               5                   10                  15

Ser Arg Gly Asn Ser Ala Ala Val Ala Pro Phe Gly Gly Leu Lys Ser
            20                  25                  30

Met Thr Gly Phe Pro Val Lys Lys Val Gln Thr Glu Ile Thr Ser Ile
        35                  40                  45

Thr Ser Glu Gly Gly Arg Val Lys Cys Met Asp Pro Val Glu Lys Ser
    50                  55                  60
```

CONSTRUCTS AND METHODS FOR ENHANCING PROTEIN LEVELS IN PHOTOSYNTHETIC ORGANISMS

RELATED APPLICATIONS

This application is a continuation-in-part of co-pending U.S. patent application Ser. No. 08/568,168, filed on Dec. 6, 1995, which is hereby incorporated in its entirety.

BACKGROUND OF THE INVENTION

All photosynthetic organisms depend on the light-harvesting reactions of photosynthesis for energy to produce important compounds for growth and metabolism. Energy-rich carbohydrates, fatty acids, sugars, essential amino acids, and other compounds synthesized by photosynthetic organisms are the basis of the food chain on which all animal life depends for existence. Photosynthetic organisms are also the major source of oxygen evolution in the atmosphere, recycling carbon dioxide in the process. Thus life on earth is reliant on the productivity of photosynthetic organisms, especially plants.

Plant productivity is limited by the amount of resources available and the ability of plants to harness these resources. The conversion of light to chemical energy requires a complex system which combines the light harvesting apparatus of pigments and proteins. The value of light energy to the plant can only be realized when it is efficiently converted into chemical energy by photosynthesis and fed into various biochemical processes.

The thylakoid protein apparatus responsible for the photosynthetic conversion of light to chemical energy is one of the most complex mechanisms in the chloroplast and remains one of the most difficult biological systems to study. Oxygen-evolving photosynthetic organisms, such as cyanobacteria, algae and plants, possess two photosystems, PSI and PSII, which cooperate in series to acquire electrons from $H_2O$ and deliver them energetically up a gradient to $NADP^+$. The photosynthetic production of NADPH and ATP then, in turn, feeds into all biochemical pathways. The force driving the uphill flow of these electrons comes from the light energy absorbed by the 100–300 chlorophyll molecules associated with the two photosystems. An important pair of chlorophyll a molecules in the center of each photosystem modulates the movement of electrons. The remaining chlorophyll molecules are associated with proteins which in turn are organized into light gathering antennae that surround the reaction centers and transfer the light energy to them (Green et al. (1991) *TIBS* 16:181).

The capacity to absorb light, especially in shade, depends largely on the size and organization of the light harvesting complexes (Lhc) in the thylakoid membranes. The LhcII light harvesting complex is the major ensemble of chlorophyll a/b binding protein (Cab) acting as an antenna to photosystem II (PSII) and plays a key role in harvesting light for photosynthesis (Kuhlbrandt, W. (1984) Nature 307:478). Plants are capable of adjusting the size of the antennae in accordance with the light intensity available for growth. In shade, the allocation of nitrogen is shifted from polypeptides in the stroma, by decreasing ribulose 1,5-bisphosphate carboxylase (Rbc or Rubisco) levels, to the thylakoidal proteins. Nitrogen redistribution is a compensating response to low irradiance, balancing light harvesting and $CO_2$ fixation (Evans, J. R. (1989) *Oecologia* 78:9); Stitt, M. (1991) *Plant, Cell and Environment* 14:741).

In addition to the shift in the investment of nitrogen into different proteins, photosynthetic organisms can adapt to low light conditions by molecular reorganization of the light harvesting complexes (Chow et al. (1990) *Proc. Natl. Acad. Sci. USA* 87:7502; Horton et al. (1994) *Plant Physiol.* 106:415; Melis, (1991) *Biochim. Biophys. Acta.* 1058:87). A plant's reorganizational ability to compensate for changes in the characteristics of the light limits its productivity. Although a mechanism is in place to adapt to low light conditions, photosynthesis in plants grown in suboptimal illumination remains significantly lower due to a limited capacity to generate ATP and NADPH via electron transport (Dietz, K. J. and Heber, U. (1984) *Biochim. Biophys. Acta.* 767:432; ibid (1986) 848:392). Under such conditions the capacity to generate ATP and NADPH, the assimilatory force, will dictate the capacity to reduce $CO_2$. When light is limiting, plants reorganize to maximize their photosynthetic capacity; however, the ability to adapt is limited by molecular parameters ranging from gene expression to complex assembly to substrate and cofactor availability.

If productivity of a plant or other photosynthetic organism is to be increased, methods to enhance the light-gathering capacity without restricting $CO_2$ fixation must be developed.

SUMMARY OF THE INVENTION

The present invention provides a chimeric gene construct comprising a promoter region, a 5' untranslated region containing a translational enhancer, DNA encoding a plastid-specific transit peptide which enhances protein import, a gene encoding a plastid protein, and a 3' untranslated region containing a functional polyadenylation signal. This construct produces a high level of expression and importation of the functional protein to the site of its function.

In one embodiment of the present invention the promoter is a 35S cauliflower mosaic virus (CaNV) promoter. In another embodiment, the translational enhancer is from the 5' untranslated region of the pea small subunit of ribulose-1,5-bisphosphate carboxylase. In another embodiment, the transit peptide is from the pea small subunit of ribulose-1,5-bisphosphate carboxylase. In a further embodiment, the gene encoding a protein is the pea cab gene, encoding a chlorophyll a/b binding protein. In yet another embodiment, the 3' untranslated region containing a functional polyadenylation signal is from the pea cab gene.

This invention also provides a method for enhancing the light harvesting capability of a photosynthetic plant or organism comprising: preparing a gene construct comprising a promoter, a 5' untranslated region containing a translational enhancer, DNA encoding a plastid-specific transit peptide which enhances protein import, DNA encoding a protein, preferably a structural gene encoding a chlorophyll a/b binding protein, and a 3' untranslated region containing a functional polyadenylation signal; inserting the gene construct into a suitable cloning vector; and transforming a photosynthetic plant or other photosynthetic organism with the recombinant vector. Alternatively, the gene construct is coated directly on biolistic particles with which the cells are bombarded.

This invention provides a DNA construct which can increase the amount of one or more proteins in a plastid, especially a chloroplast, or in the cells of photosynthetic prokaryotes. These constructs can alter the photosynthetic apparatus to increase the ability of the plant to harvest light, especially under conditions of low illumination.

This invention also provides methods of increasing the light-harvesting efficiency of photosynthesis and the yield of photosynthetic products (such as carbohydrates) in plants and other photosynthetic organisms. These methods can be used to increase the commercial value of plants and seeds, and be used to increase the yields of products produced from fermentation and plant tissue culture operations.

This invention also provides a transgenic (TR) plant or photosynthetic organism containing the construct described above. These transgenic plants and photosynthetic organisms have enhanced photosynthetic capacity and enhanced growth capabilities useful for increased yield, tissue culture, fermentation and regeneration purposes. Compared to wild-type (WT) plants, transgenic plants of this invention demonstrate increased yield, enhanced pigmentation, increased carbohydrate content, increased biomass, more uniform growth, larger seeds or fruits, increased stem girth, enhanced photosynthesis, faster germination, and increased ability to withstand transplant shock. Seeds produced from these plants are also provided by this invention, as well as plant parts useful for production of regenerated plants and other derived products.

BRIEF DESCRIPTION OF THE FIGURES

FIGS. 1A–1B is the nucleotide sequence of AB80 (pea type I LhcIIb gene) (SEQ ID NO:1) and the amino acid sequence (SEQ ID NO:2) encoded by SEQ ID NO:1.

FIG. 7A shows transgene mRNA levels in plants derived from T1 seeds of primary transformants. FIG. 7B shows transgene mRNA levels from selected T1 plants with high levels of transgene transcript that were self-crossed and subjected to segregation analysis. The resulting homozygous lines were examined in the same manner as in FIG. 7A. FIG. 7C shows the steady state Cab protein levels in transformed (TR) and wild-type (WT) tobacco plants.

FIGS. 12A–D show a comparison of WT($\nabla$) and TR($\bullet$) light response curves for photosynthetic oxygen evolution of plants cultivated in two different light intensities: (A) 50 $\mu$mol·m$^{-2}$·s$^{-1}$ (referred to as low); and (B) 500 $\mu$mol·m$^{-2}$·s$^{-1}$ (referred to as high).

DETAILED DESCRIPTION OF THE INVENTION

Figure 2:
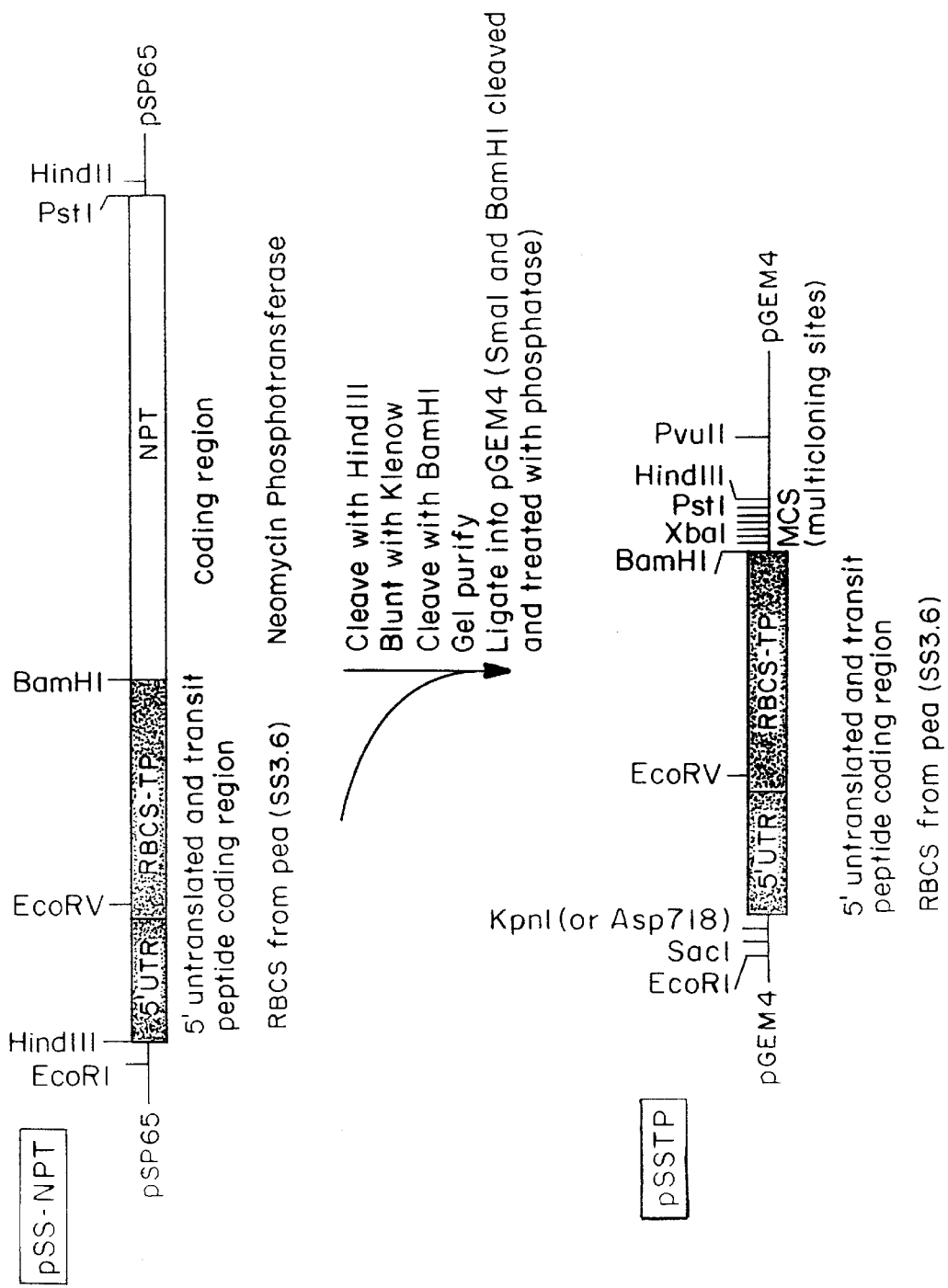
FIG. 2 shows the construction of vector pSSTP.

This invention relates to a DNA construct which, when incorporated into a plant or cell of a photosynthetic organism, increases the efficiency of plastids or a photosynthetic cell, and to methods for increasing or improving the products of plastid metabolism via enhancement of protein expression and import. The present invention also relates to transgenic plants, seeds, plant cells and tissues, and other photosynthetic organisms incorporating these constructs.

A DNA construct of this invention comprises a promoter, a 5' untranslated region containing a translational enhancer, DNA encoding a plastid-specific transit peptide which can enhance and direct import of a gene product to a plastid or photosynthetic apparatus, a gene encoding a plastid protein, and a 3' untranslated region containing a functional polyadenylation signal. Insertion of this construct results in increased expression and importation of proteins in plastids and the photosynthetic apparatus. These elements are usually provided as operably-joined components in the 5' to 3' direction of transcription. A preferred embodiment of the invention is a construct comprising a 5' constitutive promoter (such as the 35S cauliflower mosaic virus promoter), the 5' untranslated region of pea small subunit of ribulose-1,5-bisphosphate carboxylase containing a translational enhancer which has a nucleotide sequence consisting of residues 1 to 29 of SEQ ID NO:3, DNA encoding a transit peptide which is from pea small subunit of ribulose-1,5-bisphosphate carboxylase, a structural gene encoding a chlorophyll a/b binding protein and a 3' untranslated region containing a functional polyadenylation signal is from a pea cab gene.

This novel gene construction scheme permits simultaneous high level transcription, high level translation, greater mRNA stability and a high level of protein importation into the plastid or photosynthetic apparatus of an organism, producing overproduction of the selected protein (in this case, a light harvesting Cab protein) in plants and other photosynthetic organisms. The multi-level gene construction, especially the enhancement of protein importation, can be widely used to enhance the import and expression of any protein. The gene construct exemplified achieves a high level of expression and importation of the functional protein (chlorophyll a/b binding protein) at the site of its function.

The activity of many different proteins and polypeptides involved in the process of photosynthesis can be enhanced by the methods of this invention. In addition to increased levels of endogenous proteins, the DNA constructs of this invention can be used to import and express foreign proteins in the photosynthetic apparatus of plants and other photosynthetic organisms. Further, the DNA construct can contain a single protein encoding region, or can contain additional encoding regions so that several proteins can be imported and expressed. Thus, plastids of plants and cells of photosynthetic organisms can be altered to enhance the light-harvesting reactions of photosynthesis and/or to vary the level and kind of products of the photosynthetic dark reactions.

To produce the chimeric constructs provided in this invention, an effective chimeric Rbcs-Cab coding region was created by combining coding sequences for appropriate portions of Rbcs and type I LhcIIb Cab. Transgenic tobacco plants containing the gene construct of this invention overproduce type I Cab of LhcIIb and possess enhanced low light photosynthetic activity and growth capabilities. The transgenic plants also demonstrate one or more morphological, developmental, biochemical and physiological modifications. These modifications have commercial value in crop plants where more rapid germination and growth, higher yields and improved appearance are highly preferred. The desired modifications are achieved through the elevated gene expression and protein import via this novel gene construction. Enhanced expression at the level of de novo transcription was facilitated by attaching the Rbcs-Cab gene construct to the strong CaMV 35S promoter. Further enhancements were obtained by increasing mRNA stability, thus increasing the magnitude of the steady state pool of transgene transcripts. This was accomplished by inclusion of the functional 3' untranslated nucleic acid sequence of the cab gene and the nucleic acid sequence encoding the Rbcs transit peptide. Both nucleic acid sequences play a role in increasing mRNA stability. Higher levels of translation or protein synthesis were achieved by the inclusion of the Rbcs 5' untranslated sequence containing a translational enhancer, thereby increasing the pool of protein precursors for importation into the plastidic compartment. The level of Cab assembled into thylakoid membranes and LhcIIb complexes was further elevated by using a more efficient transit peptide. Switching the type I LhcIIb Cab transit peptide with the one from the small subunit of ribulose-1,5-bisphosphate carboxylase enhanced the level of import into the chloroplast. The increase in type I LhcIIb Cab content inside the chloroplast allowed the LhcIIb antennae to incorporate the extra proteins and as a result increased the size of the antennae. Any transit peptide that will cause an increase in type I LhcIIb Cab in the chloroplast by replacing the Cab transit peptide can produce in a similar elevating effect. It is also possible to achieve lower levels of importation by using less efficient transit peptides and thus regulate the amount of protein expression. The experiments described herein show that the presence of the Rbcs transit peptide enhances importation of a wide range of plastid-destined protein precursors and probably represents the highest efficiency transit peptide characterized to date.

The term "promoter" or "promoter region" refers to a sequence of DNA, usually upstream (5') to the coding region of a structural gene, which controls the expression of the coding region by providing recognition and binding sites for RNA polymerase and any other factors required for transcription to start at the correct site.

There are generally two types of promoters, inducible and constitutive promoters. The term "constitutive" as used herein does not necessarily indicate that a gene is expressed at the same level in all cell types, but that the gene is expressed in a wide range of cell types, although some variation in abundance is often detected.

An inducible promoter is a promoter that is capable of directly or indirectly activating transcription of one or more DNA sequences or genes in response to an inducer. In the absence of an inducer the DNA sequences or genes will not be transcribed. Typically a protein factor (or factors), that binds specifically to an inducible promoter to activate transcription, is present in an inactive form which is then directly or indirectly converted to an active form by the inducer. The inducer can be a chemical agent such as a protein, metabolite, growth regulator, herbicide or phenolic compound, or a physiological stress imposed directly by heat, cold, salt, or toxic elements or indirectly through the action of a pathogen or disease agent such as a virus. The inducer can also be an illumination agent such as light, darkness and light's various aspects, which include wavelength, intensity, fluence, direction and duration. A plant cell containing an inducible promoter may be exposed to an inducer by externally applying the inducer to the cell or plant such as by spraying, watering, heating or similar methods. If it is desirable to activate the expression of a gene at a particular time during plant development, the inducer can be applied at that time.

Examples of such inducible promoters include heat shock promoters, such as the inducible hsp70 heat shock promoter of *Drosphilia melanogaster* (Freeling, M. et al. (1985) *Ann. Rev. of Genetics* 19:297–323); a cold inducible promoter, such as the cold inducible promoter from *B. napus* (White, T. C. et al. (1994 *Plant Physiol.* 106:917); and the alcohol dehydrogenase promoter which is induced by ethanol (Nagao, R. T. et al., Miflin, B. J., Ed. *Oxford Surveys of Plant Molecular and Cell Biology*, Vol. 3, p 384–438, Oxford University Press, Oxford 1986).

Among sequences known to be useful in providing for constitutive gene expression are regulatory regions associated with *Agrobacterium genes*, such as nopaline synthase (Nos), mannopine synthase (Mas) or octopine synthase (Ocs), as well as regions regulating the expression of viral genes such as the 35S and 19S regions of cauliflower mosaic virus (CaMV) (Brisson et al. (1984) *Nature* 310:511–514), or the coat promoter of TMV (Takamatsu et al. (1987) *EMBO J.* 6:307–311).

Other useful plant promoters include promoters which are highly expressed in phloem and vascular tissue of plants such as the glutamine synthase promoter (Edwards et al. (1990) *Proc. Natl. Acad. Sci. USA* 87:3459–3463), the maize sucrose synthetase 1 promoter (Yang et al. (1990) *Proc. Natl. Acad. Sci. USA* 87:4144–4148), the promoter from the Rol-C gene of the TLDNA of Ri plasmid (Sagaya et al., *Plant Cell Physiol.*, 3:649–653), and the phloem-specific region of the pRVC-S-3A promoter (Aoyagi et al., *Mol. Gen. Genet.*, 213:179–185 (1988)). Alternatively, plant promoters such as the small subunit of Rubisco (Rbcs) promoter (Coruzzi et al., *EMBO J.*, 3:1671–1679 (1984); Broglie et al., *Science*, 224:838–843 (1984)), or heat shock promoters, e.g., soybean HPS17.5-E or HPS17.3-B (Gurley et al. (1989) *Mol. Cell. Biol.* 6:559–565 (1986)) may be used.

Other useful promoters which can be used according to the present invention include: the low temperature and ABA-responsive promoter Kin1, cor6.6 (Wang et al. (1995) *Plant Mol. Biol.* 28:605; Wang and Cutler (1995) *Plant Mol. Biol.* 28:619); the ABA inducible promoter from EM gene wheat (Marcotte Jr. et al. (1989) *Plant Cell* 1:969); the phloem-specific sucrose synthase promoter, ASUS1, from Arabidopsis (Martin et al. (1993) *Plant J.* 4:367); the root and shoot promoter, ACS1 (Rodrigues-Pousada et al. (1993) *Plant Cell* 5:897); the seed-specific 22 kDa zein protein promoter from maize (Unger et al. (1993) *Plant Cell* 5:831); the ps1 lectin promoter in pea (de Pater et al. (1993) *Plant Cell* 5:877); the phas promoter from *Phaseolus vulgaris* (Frisch et al. (1995) *Plant J.* 7:503); the late embryo-abundant lea promoter (Thomas, T. L. (1993) *Plant Cell* 5:1401); the fruit-specific E8 gene promoter from tomato (Cordes et al. (1989) *Plant Cell* 1:1025); the meristematic tissue-specific PCNA promoter (Kosugi et al. (1995) *Plant J.* 7:877); the NTP303 pollen-specific promoter (Weterings et al. (1995) *Plant J.* 8:55); the late embryogenesis stage-specific OSEM promoter (Hattori et al. (1995) *Plant J.* 7:913); the ADP-glucose pyrophosphorylase tissue-specific promoter for guard cells and tuber parenchyma cells (Muller-Rober et al. (1994) *Plant Cell* 6:601); the Myb conductive tissue-specific promoter (Wissenbach et al. (1993) *Plant J.* 4:411); and the plastocyanin promoter from Arabidopsis (Vorst et al. (1993) *Plant J.* 4:933).

The construct of the present invention also includes a 5' untranslated leader sequence, which acts as a translational enhancer. Specific initiation signals may be required for efficient translation of the coding sequences. These signals include the ATG initiation codon and adjacent sequences. The initiation codon must be in phase with the reading frame of the coding sequence to ensure translation of the sequence. The translation control signals and initiation codon can be of a variety of origins, both natural and synthetic. Translational control signals and initiation codon can be provided from the source of the transcriptional initiation region, or from the structural gene. This sequence can also be derived from the promoter selected to express the gene, and can be specifically modified so as to increase translation of the mRNA.

An example of a translational enhancer of the present invention is the 5' untranslated region of the pea small subunit of ribulose-1,5-bisphosphate carboxylase. Other nucleic acid sequences demonstrating translational enhancing activity have been reported for leader or 5' untranslated sequences such as from the ferrodoxin-binding protein gene psaDb (Yamamoto et al. (1995) J. Biol Chem. 270:12466), ferredoxin (Dickey et al. (1994) Plant Cell 6:1171), the 68 base leader from tobacco mosaic virus (TMV) (Gallie et al. (1987) Nucleic Acids Res. 15:3257) and the 36 base leader from alfalfa mosaic virus (Jobling et al. (1987) Nature 325:622). These translational enhancers can be used in place of the Rbcs translational enhancer signals in the present invention. Translational enhancing activity is most likely to be present in the 5' untranslated nucleic acid sequence of most other genes and their corresponding transcripts and can vary in strength and efficiency (see review by Gallie. 1993 Ann. Rev. Plant Physiol. Plant Mol. Biol. 44, 77). Such nucleic acid sequences, if demonstrated to contain translational enhancing effects, can also be used in the present invention. A translational enhancer demonstrating appropriate levels of enhancement can be selected to obtain a suitable level of translational enhancement in the constructs of the invention.

The construct of the present invention also includes a transit peptide. A "transit peptide" refers to a peptide which is capable of directing intracellular transport of a protein joined thereto to a plastid in a plant host cell. The passenger protein may be homologous or heterologous with respect to the transit peptide. Chloroplasts are the primary plastids in photosynthetic tissues, although plant cells are likely to have other kinds of plastids, including amyloplasts, chromoplasts, and leucoplasts. The transit peptide of the present invention is a transit peptide which will provide intracellular transport to the chloroplasts as well as other types of plastids. In many cases, transit peptides can also contain further information for intraorganellar targeting within the plastid to sites of function such as outer and inner envelope membranes, stroma, thylakoid membrane or thylakoid lumen. Depending on the source of the transit peptide, the precursor proteins may display differences in import behavior and import activity such as efficiency. These differences in import behavior are not attributed solely to the function of the transit peptide but also to the passenger protein and are most likely due to interactions between the two portions (Ko and Ko, 1992 J. Biol. Chem. 267, 13910). In photosynthetic prokaryotes, such as the cyanobacteria, proteins can be targeted to the photosynthetic and plasma membranes or to biochemical pathways involving the reduction of sugars and formation of photosynthetic products.

The transit peptide for the constituent polypeptide of the light-harvesting chlorophyll a/b-protein complex is rich in serine, especially near the $NH_2$-terminus, where 7 of the first 13 residues are serine. An abundance of serine also occurs near the $NH_2$-terminus of the transit peptide for the small subunit of Rbc from pea (Cashmore, A. R., Genetic Engineering of Plants, Eds. Kosuge, T. et al. (Plenum Press, New York, pp. 29–38 (1983)), soybean (Berry-Lowe, S. L. et al. (1982) J. Mol. Appl. Genet. 1:483–498), and Chlamydomonas (Schmidt, G. W. et al. (1989) J. Cell Biol. 83:615–623). Both the transit peptides for the light-harvesting chlorophyll a/b-protein complex and for the small subunit of Rbc function in the specific translocation of polypeptides across the chloroplast envelope. However, the final destination of these polypeptides is quite distinct, with the light-harvesting chlorophyll a/b-protein complex residing as integral membrane proteins in the chloroplast thylakoid and the small subunit of Rbc residing as a component of a soluble protein in the chloroplast stroma.

In one embodiment, the transit peptide is from the small subunit of Rbc. The level of Cab assembled into the thylakoid membrane and the LhcIIb complex was further elevated by using a more efficient, heterologous transit peptide. The switching of the type I LhcIIb Cab transit peptide with the one from the small subunit of ribulose-1, 5-bisphosphate carboxylase enhanced the level of Cab import into the chloroplast. The increase in type I LhcIIb Cab content inside the chloroplast allowed the LhcIIb antennae to incorporate the extra proteins and as a result increased the size of the antennae.

The gene encoding the protein to be transcribed and incorporated into a plastid or cell of a photosynthetic organism is not particularly limited. Those of skill in the art will recognize that other genes encoding pigments (such as the phycobiliproteins) or pigment-binding proteins (such as carotenoid-binding proteins) could be utilized to enhance the efficiency of the light-harvesting reactions. Many processes of photosynthesis could be similarly enhanced. For example, genes encoding the subunits of ATP synthase and ferredoxin involved in electron transport could be incorporated into the constructs of this invention to enhance electron transport. Alternatively, the expression and import of pyruvate kinase, acetyl-CoA carboxylase and acyl carrier proteins could be increased, thus amplifying a biosynthetic pathway, such as carbon/lipid metabolism.

Any gene encoding a chlorophyll a/b binding (Cab) protein can be selected as a structural gene. The chlorophyll a/b binding proteins include LhcI of four different types, LhcII of types I to III, CP29, CP26, CP24 and early light-induced proteins (Green B. R. (1991) Trends Biochem. Sci. 16:181–186). These include genes or cDNAs encoding chlorophyll a/b binding proteins that can belong to the complexes LhcIIa, LhcIIb, LhcIIc, LhcIId, LhcIIe and any other uncharacterized subcomplexes of LhcII. The same gene construction scheme can be applied as well to genes or cDNAs encoding chlorophyll a/b binding proteins of LhcI which include chlorophyll a/b binding proteins of LhcIa, LhcIb, and LhcIc of photosystem I.

LhcII is the major complex comprising the most abundant members of the family of chlorophyll a/b binding proteins, accounting for approximately 50% of total chlorophyll in the biosphere, and for the most chlorophyll b in green plants. Thus, a gene encoding a LhcII chlorophyll a/b binding protein would be a preferred gene for targeting to increase the amount of chlorophyll a/b binding proteins.

In all plant species examined to date, chlorophyll a/b binding proteins of LhcII are encoded by a multi-gene family, comprising at least five genes in Arabidopsis, six genes in *Nicotiana tabacum*, eight genes in *N. plumbaginifolia*, and up to 15 genes in tomato (Jansson, S. et al. (1992) Plant Mol. Biol. Rep. 10:242–253). Thus, any of these genes would be a suitable target for increasing the amount of chlorophyll a/b binding protein. Table 1 provides a more complete list of genes encoding chlorophyll a/b binding proteins, including those presently in the nucleic acid sequence data banks such as that represented and listed in Table 2 of the publication by Jansson, et al. (1992) supra.

TABLE 1

Genes encoding chlorophyll a/b binding proteins, and their relation to designations for chlorophyll-protein complexes Gene Product/Pigment-Protein Complex

| Gene | Green et al. 1991 Trends Biochem Sci. 16, 181 | Thornber et al. 1991 | Bassi et al. 1990 | References (genes) | References (proteins) |
|---|---|---|---|---|---|
| Lhca 1 | Type I LhcI | Lhc Ib | LhcI-730 | Hoffman et al., 1987 Jansson & Gustafsson 1991 Palomares et al., 1991 | Ikeuchi et al., 1991 Knoetzel et al., 1992 |
| Lhca 2 | Type II LhcI | Lhc Ia | LhcI-680 | Stayton et al., 1987 Pichersky et al., 1988 Jansson & Gustafsson 1991 | Ikeuchi et al., 1991 Knoetzel et al., 1992 |
| Lhca 3 | Type III LhcI | Lhc Ia | LhcI-680 | Pichersky et al., 1989 Jansson & Gustafsson 1991 | Ikeuchi et al., 1991 Knoetzel et al. 1992 |
| Lhca 4 | Type IV LhcI | Lhc Ib | LhcI-730 | Schwartz et al., 1991a Zhang et al., 1991 | Ikeuchi et al., 1991 Schwartz et al., 1991a Knoetzel et al. 1992 |
| Lhcb 1 | Type I LhcII | Lhc IIb 28 kDa | LhcII | Chitnis & Thornber, 1988* | Jansson et al., 1990 Green et al., 1992 |
| Lhcb 2 | Type II LhcII | Lhc IIb 27 kDa | LhcII | Chitnis & Thornber, 1988* | Jansson et al., 1990 Green et al., 1992 |
| Lhcb 3 | Type III LhcII | Lhc IIb 25 kDa | LhcIIa | Schwartz et al., 1991b Brandt et al., 1992 | Bassi & Dainese, 1990 Morishige & Thornber, 1991 Bassi & Dainese, 1992 Green et al., 1992 |
| Lhcb 4 | Type II CP29 | Lhc IIa | CP29 | Morishige & Thornber, 1992 | Henrysson et al., 1989 Pichersky et al., 1991 Morishige & Thornber, 1992 |
| Lhcb 5 | Type I CP29 | Lhc IIc | CP24 | Pichersky et al., 1991 Sorenson et al., 1992 | Pichersky et al., 1991 Morishige & Thornber, 1992 |
| Lhcb 6 | CP24 | Lhc IId | LhcI-730 | Schwartz & Pichersky, 1990 | Morishige et al., 1990 Spangfort et al., 1990 |

*Because numerous genes of these kinds have been cloned and sequenced, a review article is given as reference.
REFERENCES:
Green et al. 1991, Trends Biochem. Sci. 16, 181.
Thornber et al. 1991, In: Chlorophylls. Scheer, H. (ed.) CRC Press pp. 549–585.
Bassi et al. 1990, Photochem. Phototbiol. 52, 1187.
Hoffman et al. 1987, Proc. Natl. Acad. Sci. USA 84, 8844.
Jansson & Gustafsson, 1991. Mol. Gen. Genet. 229, 67.
Palomares et al. 1991, J. Photochem. Photobiol. B: Biol. 11, 151.
Ikeuchi et al. 1991, Plant Cell Physiol. 32, 103.
Knoetzel et al. 1992, Eur. J. Biochem 206, 209.
Stayton et al. 1987, Plant Mol. Biol. 10, 127.
Pichersky et al. 1988, Plant Mol. Biol. 11, 69.
Pichersky et al. 1989, Plant Mol. Biol. 12, 257.
Schwartz et al. 1991a, FEBS Lett. 280, 229.
Zhang et al. 1991, Plant Physiol 96, 1387.
Chitnis and Thornber, 1988, Plant Mol. Biol. 11, 95.
Jansson et al. 1990, Biochim. Biophys. Acta. 1019, 110.
Green et al. 1992, FEBS Lett. 305, 18.
Schwartz et al. 1991b, Plant Mol. Biol. 17, 923.
Brandt et al. 1992, Plant Mol. Biol. 19, 699.
Bassi & Dainese, 1990, In: Current Research in Photosynthesis. Vol II, Baltscheffsky, M. (ed.) pp 209–216.
Morishige & Thornber, 1991, FEBS Lett. 293:183.
Bassi & Dainese, 1992, In: Regulation of chloroplast biogenesis. Argyroudi-Akoyonoglou, J. (ed.) pp. 511 . 520.
Morishige & Thornber, 1992, Plant Physiol. 98, 238.
Henrysson et al. 1989, Biochim. Biophys. Acta. 977, 301.
Pichersky et al. 1991., Mol. Gen. Genet. 227, 277.
Sorensen et al. 1992, Plant Physiol. 98, 1538.
Schwartz & Pichersky, 1990. Plant Mol. Biol. 15, 157
Morishige et al. 1990. FEBS Lett. 264, 239
Spangfort et al. 1990. In: Current Research in Photosynthesis. Vol II, Baltscheffsky, M. (ed.) pp 253–256.

The Cab protein of PSII encoded by ICABPSII is the major light harvesting antenna associated with PSII and contains 40–60% of the total chlorophyll in the mature chloroplast (Boardman et al. (1978) *Current Topics in Bioenergetics*, 8:35–109). Further, within PSII, there is a very high sequence homology between type I and type II Cab proteins (Pichersky et al. (1989) *Plant Mol. Biol.* 12:257). Thus, targeting this gene will significantly alter the chlorophyll content.

Useful genes encoding a chlorophyll a/b binding protein, which can be used according to the present invention, include:

a) the light harvesting complex I—complexes of photosystem I, such as Lhca1 type I, the major Cab proteins of PSI, e.g. Lhca1*1 (Hoffman et al. (1987) *Proc. Natl. Acad. Sci. USA* 84:8844); Lhca2; Lhca3 type III, the major Cab proteins of PSI, e.g. Lhca3*1 (Pichersky et al. (1989) *Plant Mol. Biol.* 12:257); Lhca4; and b) the light harvesting complex II—complexes of photosystem II, such as Lhcb1; Lhcb2 type II, the major Cab proteins, e.g. Lhcb2*1 (Pichersky et al. (1987) *Plant Mol. Biol.* 9:109); Lhcb3 type III, the major Cab proteins, e.g. Lhcb3*1 (Schwartz et al. (1991) *FEBS Lett.* 280:229); Lhcb4; Lhcb5; and Lhcb6.

In one embodiment of the present invention, a nuclear gene encoding a constituent polypeptide of the light-harvesting chlorophyll a/b protein complex (type I Lhc IIb), which has been isolated from pea (*Pisum sativum*) (Cashmore, A. R. (1984) *Proc. Natl. Acad. Sci. USA* 81:2960–2964) was used. In other embodiments, the cab genes selected can represent the remaining two proteins of LhcIIb or other major proteins of LhcIb. In addition to type I, there are two other Cab proteins of LhcIIb: type II and type III. Since these two proteins are constituents of the major light harvesting complex LhcIIb, they may also play an important role in low light and may also be preferred. The LhcIb complex is the major complex for photosystem I and consists of two Cab proteins, type I and III LhcIb Cab.

The construct of the present invention further comprises a 3' untranslated region. A 3' untranslated region refers to that portion of a gene comprising a DNA segment that includes a polyadenylation signal and can include other regulatory signals capable of affecting mRNA processing, mRNA stability, or gene expression. The polyadenylation signal is usually characterized by effecting the addition of a polyadenylic acid tract to the 3' end of the mRNA precursor. Polyadenylation signals are commonly recognized by the presence of homology to the canonical form 5' AATAAA-3' although variations are not uncommon.

Examples of suitable 3' regions are the 3' transcribed non-translated regions containing a polyadenylation signal of Agrobacterium tumor inducing (Ti) plasmid genes, such as the nopaline synthase (Nos gene) and plant genes such as the soybean storage protein genes and the gene for the small subunit of ribulose-1,5-bisphosphate carboxylase. Other suitable 3' sequences may be derived from any characterized gene from plants as well as from other organisms such as animals if they are deemed appropriately functional in the environment of a transgenic plant cell or cell of a photosynthetic organism. In one embodiment of the invention, the 3' untranslated region is derived from the structural gene of the present construct.

When specific sequences are referred to in the present invention, it is understood that these sequences include within their scope, sequences which are "substantially similar" to the specific sequences. Sequences are "substantially similar" when at least about 80%, preferably at least about 90% and most preferably at least about 95% of the nucleotides match over a defined length of the molecule. Sequences that are "substantially similar" include any sequence which is altered to contain a substitution, deletion, or addition of nucleotides compared to the sequences of this invention, especially substitutions which rely on the degeneracy of the genetic code, and which have similar characteristics (i.e., function). DNA sequences that are substantially similar can be identified and isolated by hybridization under high or moderate stringency conditions, for example, which are chosen so as to not permit the hybridization of nucleic acids having non-complementary sequences. "Stringency conditions" for hybridization is a term of art which refers to the conditions of temperature and buffer concentration which permit hybridization of a particular nucleic acid to another nucleic acid in which the first nucleic acid may be perfectly complementary to the second, or the first and second may share some degree of complementarity which is less than perfect. "High stringency conditions" and "moderate stringency conditions" for nucleic acid hybridizations are explained on pages 2.10.1–2.10.16 and pages 6.3.1–6 in *Current Protocols in Molecular Biology* (Ausubel, F. M. et al., eds., Vol.1, containing supplements up through Supplement 29, 1995), the teachings of which are hereby incorporated by reference.

To aid in identification of transformed plant cells, the constructs of this invention may be further manipulated to include genes coding for plant selectable markers. Useful selectable markers include enzymes which provide for resistance to an antibiotic such as gentamycin, hygromycin, kanamycin, or the like. Similarly, enzymes providing for production of a compound identifiable by color change such as GUS (β-glucuronidase), or by luminescence, such as luciferase, are useful.

The constructs of the present invention can be introduced into plant cells through infection with viruses or bacteria or direct introduction by physical or chemical means. Examples of indirect (infection) and direct methods include Ti plasmids, Ri plasmids, plant virus vectors, microinjection, microprojectiles, electroporation, and the like. For reviews of such techniques see, e.g., Weissbach and Weissbach, *Methods for Plant Molecular Biology*, Academic Press, New York, Section VIII, pp. 421–463 (1988); and Grierson and Corey, *Plant Molecular Biology*, 2d Ed., Blackie, London, Ch. 7–9 (1988). The term "transformation" as used herein, refers to the insertion of a construct into a plant cell or the cell of a photosynthetic organism by any of the above methods.

Methods of regenerating whole plants from plant cells are known in the art (See, e.g., *Plant Molecular Biology Manual*, (Eds. S. B. Gelvin, R. A. Schilperoort) Kluwer Acad. Publishers (1988)), and the method of obtaining transformed and regenerated plants is not critical to this invention. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques.

Also considered part of this invention are plants and other photosynthetic organisms containing the nucleic acid construct of this invention. Suitable plants include both monocotyledons and dicotyledons, as well as gymnosperms and lower plants (e.g., ferns, bryophytes) included in the kingdom Plantae, and lichens. Examples of preferred monocotyledons include rice, corn, wheat, rye and sorghum. Examples of preferred dicotyledons include canola, pea, soybeans, sunflower, tobacco, cotton, sugar beet, petunia, tomato, broccoli, lettuce, apple, plum, orange, lemon, and rose. Other photosynthetic organisms can also be used as hosts for the construct of the present invention. These include the single-celled eukaryotic and multicellular algae, such as Porphyra sp., *Chondrus crispus*, Gigartina sp., Eucheuma sp., Laminaria sp., Macrocystis sp., *Nereocystis leutkeana, Chlamydomonas reinhardtii, chlamydomonas moewusii, Euglena gracilis*, Cryptomonas Φ, and *Ochromonas sinensis*. This invention also includes prokaryotes which lack plastids but have a photosynthetic apparatus, such as the cyanobacteria (blue-green algae) and photosynthetic microbes, which include, for example, *Anacystis nidulans*, Spirulina sp., Synechococcus sp., *Rhodobacter sphaeroides, Rhodobacter capsulatus, Chloroflexus aurantiacus*, and *Heliobacterium chlorum*. Those of skill in the art can recognize the examples given above are not limiting.

Transgenic plants can be used to provide plant parts according to the invention for regeneration or tissue culture of cells or tissues containing the constructs described herein. Plant parts for these purposes can include leaves, stems, roots, flowers, tissues, epicotyl, meristems, hypocotyls, cotyledons, pollen, ovaries, cells, and protoplasts, or any other portion of the plant which can be used to regenerate additional transgenic plants, cells, protoplasts or tissue culture.

Seed of transgenic plants are provided by this invention and can be used to propagate more plants containing the constructs of this invention. These descendants are intended to be included in the scope of this invention if they contain the constructs of this invention, whether or not these plants are selfed or crossed with different varieties of plants.

The constructs of this invention provide materials and methods through which genetic improvements in crop cultivars can be made to produce a substantial enhancement in productivity and the economic value of crops. Most of the experimental strategies in the agribiotechnology and agricultural industries are aimed at enhancing the productivity of crop plants to maximize the returns per unit of farmland. Although the preferred approach is to increase yield directly, productivity can also be enhanced by indirect means, such as reduction of input cost (e.g., fertilizers and water) or by reducing losses due to disease, insects and competition. These indirect results can be effected by incorporating novel traits into crop plants that will lower the need for fertilizers, confer disease resistance, repel damaging insects or sustain herbicides. Increases in productivity can also result from improving the adaptability of the plant to other unfavorable environmental conditions. Further increases can be achieved by combinations of these traits, through the use of molecular procedures and making hybrids.

Most molecular attempts to alter photosynthesis, both direct and indirect, have resulted in the inhibition of photosynthesis. These studies are reviewed by Furbank and Taylor (1995) *Plant Cell* 7:797 and Stitt and Sonnewald (1995) *Ann. Rev. Plant Physiol. Plant Mol. Biol.* 46:341. The methods used primarily involved reduction, via antisense transgenes, of enzymes involved in photosynthetically-related processes. Ko et al. (1992 *Research in Photosynthesis Vol III: Proceedings of the IXth International Congress on Photosynthesis*, Ed. N. Murata.

Kluwer Academic Press, pp. 445–448) demonstrated a positive functional change to tobacco.

The organizational diversity of the light-harvesting complexes and the Cab proteins involved suggests that variations in molecular relationships between different light harvesting complexes/proteins is one of the key mechanisms of the plant's adaptability to changing light conditions. For instance, a possible reorganizational event to cause adaptation to low lighting conditions could simply be the enlargement of the light harvesting complexes to gather more light by virtue of antennae size or surface area. Larger antennae would capture more light for conversion to chemical energy. Therefore enhancement of the plant's flexibility to reorganize the light harvesting machinery in response to varying light conditions can benefit the plant. Limitations on flexibility can be due to limiting levels of functional Cab proteins expressed in the plants; therefore elevations in the levels of Cab proteins will relieve the limitations. Relieving these molecular limitations can result in significant changes to photosynthesis and interrelated activities and processes, giving rise to changes to productivity and yield and improvements in the marketability and value of plant and other products from crop plants. For instance, genetic modifications aimed at enhancing photosynthesis are especially important in situations where crop production must be profitable despite the limitations imposed by diverse environmental conditions, e.g., limiting light conditions. Enhancing photosynthesis and related activities can also have a significant impact on crops engineered to produce non-plant products, e.g., health products, by providing the energy to drive the production of such products. The implications of this type of directed genetic modification approach are diverse and cannot be listed individually or estimated as a single economic benefit. Impact of this work can be significant, from improved crop productivity to indirect savings due to reduction in the lighting requirements of greenhouse grown plants. The technology applies not only to crop plants but also to horticultural plants, from house plants to orchids to ornamentals. Due to the universality of the photosynthetic process being enhanced, the technology is most likely to be beneficial and applicable to all photosynthetic organisms and plant varieties. In addition to the advancement of knowledge of photosynthesis and related activities, there are four principal categories of benefits to agriculture and horticulture provided by this invention:

1) Improved marketability of plant products (e.g., greener plants);
2) Improved productivity under low light conditions;
3) Improved planting density; and
4) Improved yields.

The development of technologies for the transfer of genes into plant cells and regeneration of intact and fertile plants from the transformed cells provides methods to modify certain of these molecular parameters to provide flexibility for the enhancement of a plant's photosynthetic capacity in low light. Overproduction and elevation of functional Cab proteins of the light harvesting antennae of photosystem II enable a plant to reorganize and harvest more light for photosynthesis. Modifications which cause a positive effect on photosynthesis can give rise to new desirable traits that have widespread benefits in agriculture and horticulture. These novel traits in the form of genetically engineered plants can provide plants with advantages in the field, greenhouse or any other form of growing practice compared with their normal unaltered counterparts. Advantageous traits can also be introduced through traditional breeding strategies to provide any desirable recombinant plant lines, e.g., elite lines, with the beneficial novel traits in addition to established desirable agronomically important phenotypes.

In particular, enhancing chlorophyll binding proteins in plastids can produce a higher chlorophyll content in plastids. Greener plants have commercial value in horticulture, both in the production of potted plants for house and garden, and for landscaping purposes. The improved color and growth resulting from incorporation of the constructs of this invention can provide superior phenotypes in all varieties of plants, including turf grasses, ground covers, flowers, vegetables, trees and shrubs. Further, elevated chlorophyll levels will produce post-harvest color retention for fresh produce or dried plant products. Increased pigments levels of carotenoids and phycobiliproteins can also have commercial value for the same purposes. Further, increased levels of carotenoids can lead to increased nutritive value in foods such as carrots, and can increase resistance of plants to the damaging effects of ultraviolet light.

The transgenic plants of this invention demonstrate many other improved properties. Transgenic plants are bigger than their wild-type counterparts, even under high light conditions. Following inclusion of a gene encoding the Cab binding protein, they are greener and demonstrate more robust growth than wild-type plants. The constructs of this invention can also provide plants with a means to withstand transplantation shock. Transplanted transgenic plants recover from the setbacks of transplanting more rapidly than wild-type plants.

Seeds of transgenic plants are larger and germinate more rapidly than seeds produced by wild-type plants, forming more robust seedlings. Faster germination results in larger shoots and extensive roots which are less susceptible to the fungal and bacterial pathogens that attack germinating seeds and seedlings. Further, seedlings which quickly establish extensive and deep root systems are more resistant to drought stress. Thus, transgenic seeds and seedlings are more commercially valuable than naturally-occurring varieties.

Further, the constructs and methods of this invention can be used to enhance stem girth, thereby enhancing support of a plant. This is especially valuable for fruit bearing crops such as tomatoes, pears, apples, oranges, lemons, and the like. Larger and sturdier stems will permit the development of varieties that can bear and support more fruit. Further, newly-transplanted ornamental plants, including trees and small shrubs subject to wind can benefit from enhanced stem girth for support until they establish strong root systems.

The growth benefits afforded to transgenic plants and plant cells of this invention can be reproduced by incorporating the constructs of this invention into single-celled photosynthetic organisms and plant tissue culture. Thus, more rapid production of plant products which are not easily synthesized, such as taxol and other cell wall products, which are produced in slow-growing plants and in tissue culture, can be realized. Further, increased photosynthesis and the subsequent increase in growth under low light intensities means that plant regeneration can be accelerated and illumination can be reduced for tissue culture and plant production.

In fact, the reduced light requirement of plants described in this invention can permit these plants to be grown at lower cost in low light facilities such as caves (currently used in the floral industry) and under denser canopies. More highly developed technological uses include chambers associated with life support systems for space travel. Space agencies would like to enhance the growth of photosynthetic organisms, and lower light requirements of such organisms would make such a system easier and less expensive to manufacture and operate.

One especially useful embodiment of this invention is the production of shade-tolerant varieties of grasses. These varieties can be planted where present varieties will not grow due to reduced illumination levels. This includes, for example, portions of lawns shaded by trees, as well as indoor stadiums where astroturf is now required because of light limitations. NFL football teams are currently converting outdoor stadium fields from Astroturf to living grass due to Astroturf-related injuries. Indoor stadium fields are under light-limiting domes, however, and grass cannot be grown in these fields unless a more shade-tolerant variety is provided.

In another aspect of this invention, the constructs of this invention can be used to produce plants with less variability in their growth pattern. Transgenic plants provided by this invention grow more evenly than wild-type plants under both greenhouse and field conditions because the available light is used effectively by all parts of the plants. This characteristic can produce yield advantages in commercially-grown plants such as corn or soybeans, where the lower shaded leaves can grow more vigorously, producing an increased biomass which not only contributes to seed yield but also shades out weeds.

The DNA construct provided by this invention can be used as a plant transformation marker, based on differences in coloration, shade/low light responses and faster growth and/or development, especially under low light conditions. The use of naturally-occurring plant DNA sequences allows the detection of integration of exogenous DNA constructs in photosynthetic cells and organisms without the regulatory problems associated with foreign selectable markers. In particular, there is provided a method for detecting transformation in plants, plant tissue or a photosynthetic organism consisting of: preparing a DNA construct comprising a promoter region, a 5' untranslated region containing a translational enhancer, a plastid-specific transit peptide, a gene encoding a plastid protein the expression of which is detectable, and a 3' untranslated region containing a functional polyadenylation signal; inserting the DNA construct into a cloning vector; and transforming a plant, tissue culture or photosynthetic organism with the cloning vector so that the protein is expressed, wherein expression of the protein is indicative of transformation. Preferably, expression and import of the protein into plastids or to the photosynthetic apparatus of cells are increased relative to wild-type plastids and cells. In one embodiment, the encoded protein is chlorophyll a/b binding protein.

The marker gene which is expressed can provide a visibly reactive response, i.e., cause a distinctive appearance or growth pattern relative to plants or cells of photosynthetic organisms not expressing the selectable marker gene, allowing them to be distinguished from other plants, parts of plants, and cells of photosynthetic organisms for purposes of identification. Such a characteristic phenotype (e.g., greener cells) allows the identification of protoplasts, cells, cell groups, tissues, organs, plant parts or whole plants containing the constructs. Green pigmentation in cells can be easily measured and screened by using techniques such as FACS (fluorescence-activated cell sorting). Galbraith, D. W. (1990) *Methods Cell Biol.* 33:547–547. If another gene has been incorporated with the construct, detection of the marker phenotype makes possible the selection of cells having a second gene to which the marker gene has been linked. This second gene typically comprises a desirable phenotype which is not readily identifiable in transformed cells, but which is present when the plant cell or derivative thereof is grown to maturity, even under conditions wherein the selectable marker phenotype itself is not apparent.

The following examples describe specific aspects of the invention to depict the invention and provide a description of the methods used to provide the constructs of the invention and to identify their function in organisms. The examples should not be construed as limiting the invention in any way.

EXEMPLIFICATION

Example 1
In vitro Translation and Protein Import Analysis

A variety of different gene fusions were prepared which demonstrate that the Rbcs 5' untranslated region (5'UTR) and the Rbcs transit peptide confer higher levels of translation and importation, respectively, of chimeric gene constructs. These in vitro import assay and translation data are summarized in Table 2. In many cases, the Rbcs transit peptide conferred higher levels of import for the passenger protein into the chloroplast. The translation-enhancing effect of the 5'URT of the Rbcs gene was demonstrated in an in vitro wheat germ translation system. These data show the Rbcs 5'URT is a translational enhancer by definition.

The analysis of protein importation and related aspects, such as efficiency, was carried out using in vitro radiolabelled proteins and in vitro import assays. Radiolabelled proteins were synthesized from corresponding DNA templates via transcription and are depicted in Table 2. All transcription plasmids depicted were propagated in the *Escherichia coli* strains HB101 or the JM101-109 strain series. The transformation of various bacterial strains was carried out using standard protocols (see, e.g., *Molecular Cloning: A Laboratory Manual*, Sambrook et al. 1989, Cold Spring Harbor Laboratory, Cold Spring Harbor, N.Y.). Plasmid DNA was isolated from the bacterial strains harboring the corresponding plasmids using standard protocols (Sambrook et al. 1989, supra). A variety of transcription plasmids containing different fusions (Table 2) were linearized at appropriate restriction sites 3' to the gene fusion DNA template. Restriction enzyme digestion buffers and digestion conditions were employed according to the protocols provided by the supplier of each particular enzyme. The gene fusion templates can be created, inserted and propagated in a variety of commercially available transcription plasmids such as the pBLUESCRIPT series (Stratagene), the pBS series (Stratagene), the pGEM and pSP series (Promega) and pT7/T3 series (Pharmacia). Transcription plasmids usually contain multiple cloning regions for cloning manipulations and at least one of the viral RNA polymerase promoters. These promoters can be, for example, T7, T3 or SP6, which use the corresponding RNA polymerase.

Restriction enzyme was added to give 5–10 units per microgram of DNA and the reaction mixture was adjusted to the appropriate final volume with water. The final volumes were usually 200 $\mu$l and contained 10 $\mu$g of plasmid DNA. Digestions were thoroughly mixed and carried out for 1–3 h at the appropriate suggested temperature. Digested templates were re-purified by phenol and chloroform:isoamyl alcohol extraction, centrifugation (usually in a microfuge) and the aqueous layer containing the digested DNA concentrated by precipitation in two volumes of 100% ethanol in the presence of 0.3 M sodium acetate, pH 7.0. The phenol used was saturated with 0.1 M Tris-HCl pH 8.0 plus 0.1% (w/v) hydroxquinoline prior to use. The chloroform:isoamyl alcohol consisted of 24 volumes of chloroform and 1 volume of isoamyl alcohol. Equal volumes of aqueous reaction mixture and phenol or chloroform:isoamyl alcohol were used in each of the organic solvent extraction steps. The DNA precipitates were collected by centrifugation, washed once with 70% (v/v) ethanol, dried and redissolved in a volume of 20 $\mu$l water prior to in vitro transcription.

The templates were transcribed in vitro using the appropriate RNA polymerase corresponding to the promoter type according to Melton et al. (1984) *Nucl. Acids Res.* 12:7035. An unmethylated cap analog (GpppG), usually at a concentration of 0.5 mM (Pharmacia), was included in the reactions. A typical transcription reaction (200 $\mu$l total volume) consisted of DNA template (5 $\mu$g), RNA polymerase (40 units of either SP6, T3 or T7), transcription reaction buffer (final concentration of 40 mM Tris-HCl pH 7.5, 6 mM $MgCl_2$, 2 mM spermidine, 10 mM NaCl), dithiothreitol (DTT, 5 mM), 40 units RNasin, and 0.25 mM of ATP, GTP, CTP and UTP. The transcripts were re-purified by phenol and chloroform:isoamyl alcohol extraction, centrifugation and the aqueous layer containing the RNA transcripts concentrated by precipitation with 750 $\mu$l of 100% ethanol in the presence of 0.3 M potassium acetate pH 7.0. The transcripts (330 $\mu$l of the reaction) were concentrated after precipitation in ethanol by centrifugation, washed with 70% (v/v) ethanol/water, dried and redissolved in 34 $\mu$l of water in the presence of 20–40 units of RNasin. Alternatively the transcript precipitates were stored at −70° C. until use.

The transcripts were then translated in a wheat germ extract system containing either $^{35}$S-radiolabelled methionine (New England Nuclear or Amersham) or TRAN$^{35}$S-Label (ICN) which contains both radiolabelled methionine and cysteine. Wheat germ extracts were prepared according to Erickson and Blobel (1983) *Methods in Enzymol.* 96:38 with some modifications. The wheat germ extract was prepared by grinding 3 g of untoasted wheat germ (General Mills, Inc., Minneapolis, Minn.) using a mortar and pestle in the presence of liquid nitrogen. Grinding proceeded until a fine powder was achieved. The powdered wheat germ was then transferred to a second prechilled mortar where grinding continued in the presence of 12 ml homogenization buffer (100 mM potassium acetate, 40 mM Hepes-KOH pH 7.6, 4 mM DTT, 2 mM $CaCl_2$, 1 mM magnesium acetate) until the mixture had a thick paste consistency. The homogenate was then transferred to 30 ml Corex tubes and centrifuged for min at 31,000×g at 4° C. The supernatant was recovered and centrifuged in a 15 ml Corex tube for another 10 min at the same g force. The final supernatant was carefully removed and its volume determined (typically 8–9 ml). The supernatant was loaded onto a Sephadex G-25 Fine (Pharmacia) column (2.5×20 cm) which was pre-sterilized by autoclaving. The column consisted of 20 g (giving a column bed of 2.5×18 cm) of Sephadex G-25 Fine (Pharmacia, Sigma) presoaked overnight with chilled, sterilized water and equilibrated with column buffer (100 mM potassium acetate, 40 mM Hepes-KOH pH 7.6, 4 mM DTT, 5 mM magnesium acetate) before use. The wheat germ extract was eluted at a rate of 1–1.5 ml/min with column buffer and fractions were collected when the leading brown band migrated two-thirds down the column. The protein content of each fraction was monitored by measuring absorbance at 280 nm in a spectrophotometer. The fractions encompassing the first peak were pooled and mixed. Aliquots of this first eluted peak were quick-frozen in liquid nitrogen and stored at −70° C. until use. A typical translation reaction consisted of transcript from 330 $\mu$l of ethanol precipitate dissolved in 34 $\mu$l water, 20–40 units of RNasin, 5–6 mM ATP, 0.4 mM GTP, 64 mM creatine phosphate, 0.08–0.09 mM of each amino acid, except that either methionine or methionine plus cysteine was not added, depending on the type of $^{35}$S labelled amino acid(s) used, 4–8 units creatine phosphokinase, compensation buffer (final concentration: 100 mM potassium acetate pH 7.0, 2 mM DTT, 0.3 mM magnesium acetate, 0.8 mM spermidine) and wheat germ extract (80 $\mu$l in a 200 $\mu$l reaction). The amount of radiolabelled amino acid used in the translations was based on radiolabelled methionine alone in the amount of 200 $\mu$Ci per reaction. The translation reactions were carried out for 1.5 h at 26–27° C. and the translation products normally analyzed prior to import assays or other related experimentation by SDS-polyacrylamide gel electrophoresis (SDS-PAGE) and fluorography. The amount of radiolabel incorporation was determined by counting TCA-precipitable radioactive counts of 1 $\mu$l samples of each translation reaction.

The intact chloroplasts used in the import assays were purified from pea seedlings (cv. Improved Laxton's Progress) as described by Bartlett et al. (1982) *Methods in Chloroplast Molecular Biology*, (eds. Edelman et al.) pp. 1081–1091 or Cline et al. (1985) *J. Biol. Chem.* 260:3691). The growth conditions were identical to those described previously (Ko and Cashmore (1989) *EMBO J.* 8:3187). Pea seedlings from 200 g of seeds were grown for 9–11 days in growth chambers set at 21° C. under fluorescent lighting with 16:8 h light:dark photoperiod. Pea seedlings were harvested and homogenized in cold grinding buffer (50 mM Hepes-KOH pH 7.6, 0.33 M sorbitol, 0.05% (w/v) bovine serum albumin (BSA), 0.1% (w/v) ascorbate, 1 mM MgCl$_2$, 1 mM MnCl$_2$, 2 mM Na$_2$EDTA) for 2–3 brief blendings of 5–10 sec at a setting of 5–6 on a Polytron Homogenizer. All steps were conducted at approximately 4° C. The homogenate was then filtered through three layers of Miracloth and the crude chloroplasts collected by centrifugation at 2,800×g for 3 min at 4° C. The crude chloroplast pellet was resuspended in 4 ml of grinding buffer and layered onto a 10–80% Percoll gradient (50 mM Hepes-KOH pH 7.6, 0.33 M sorbitol, 0.05% (w/v) BSA, 0.1% (w/v) ascorbate, 0.15% (w/v) polyethylene glycol, 0.05% (w/v) Ficoll, 0.02% (w/v) glutathione, 1 mM MgCl$_2$, 1 mM MnCl$_2$, 2 mM Na$_2$EDTA and Percoll). The gradients were centrifuged in a swing out rotor at 10,000×g for 10 min at 4° C. and the intact chloroplast band near the bottom of the gradient was collected and diluted at least five fold with 1× HS buffer (50 mM Hepes-KOH pH 8.0, 0.33 M sorbitol). The intact plastids were collected by centrifugation at 4,350×g for 2 min. This step was repeated with the pelleted chloroplasts by resuspending in 1× HS. The final pellet was resuspended in 5 ml of 1× HS and an aliquot subjected to chlorophyll analysis. Chlorophyll assays were performed as described by Arnon (1949) *Plant Physiol.* 24:1. Samples were extracted with 80% (v/v) acetone/20% water. Insoluble material was removed by centrifugation in a microfuge for 1 min at high speed. The supernatant was removed for spectrophotometric analysis of chlorophyll according to the Arnon conversion equation.

The in vitro import assays were performed in 0.3 ml volumes as described by Bartlett et al. (1982) *Methods in Chloroplast Molecular Biology*, eds. Edelman et al., pp. 1081–1091. The reactions typically contained an equivalent of 100 $\mu$g chlorophyll of chloroplasts; $^{35}$S-radiolabelled translation products adjusted to 1× HS, 10 mM methionine, mM cysteine (when TRAN$^{35}$S-Label was used) and import buffer (1× HS). The samples were shaken gently for 30 min at room temperature under fluorescent lights. Import assays can alternatively be carried out using exogenously added ATP instead of light-driven ATP synthesis. Typically, amounts such as 1 mM-3 mM ATP can be added. Intact chloroplasts were re-isolated for further treatment and subfractionation according to the scheme described by Smeekens et al. (1986) *Cell* 46:365. After the reaction, the chloroplasts in the import assays were collected by centrifugation at 686×g for 3 min, resuspended in 500 $\mu$l 1× HS, treated with thermolysin (final concentration 1 $\mu$g/$\mu$l) and re-isolated through 40% Percoll cushions by centrifugation at 1,940×g for 4 min. The intact chloroplasts were collected at the bottom of the tube and resuspended in 500 $\mu$l 1× HS, washed once by centrifugation at 686×g for 3 min and resuspended in 50 $\mu$l of solution A (0.1 M Na$_2$CO$_3$, 0.1 M β-mercaptoethanol). Five $\mu$l samples were removed from each import reaction for chlorophyll analysis as described above. The chlorophyll content was used to normalize the samples before loading on protein gels. The resuspended chloroplasts pellets were then prepared for SDS-PAGE by adding 30 $\mu$l solution B (5% (w/v) SDS, 30% (w/v) sucrose, 0.1% (w/v) bromophenol blue) and boiled for 30 sec. Aliquots from in vitro wheat germ translations and the various import reactions were analyzed by SDS-PAGE employing appropriate gel density percentages (Laemmli, (1970) *Nature* 227:80). After electrophoresis, the gels were prepared for fluorography using ENHANCE™ (New England Nuclear) according to the manufacturer's instructions and exposed to Kodak XAR™ X-ray film. Import levels and distribution of imported products were calculated from the fluorograms using an LKB ULTRASCAN XL Laser densitometer. The results of the protein fusions are summarized in Table 2.

TABLE 2

Summary of in vitro import and translation results for various constructs

A) Plants

| Promoter | Translational Enhancer | Transit Signal | Passenger | Phenotype | Protein Level | Comments |
|---|---|---|---|---|---|---|
| 35SCaMV | Rbcs[1] | Rbcs | Cab[2] | + | >Cab | Enhanced low light photosynthesis |
| 35SCaMV | Cab | Cab | Cab | 0 | =Cab | Normal photosynthesis |

B) Test tube studies

| Promoter | Translational Enhancer | Transit Signal | Passenger | Translation | Import Level | Comments |
|---|---|---|---|---|---|---|
| — | Rbcs | Rbcs | Rbcs | high | high | normal for Rbcs |
| — | Rbcs | Rbcs | Cab | high | high | 50% higher than Cab alone |
| — | Cab | Cab | Cab | good/high | good | normal for Cab |
| — | Cab | Cab | Rbcs | good/high | good | 50% lower than Rbcs alone |
| — | Oee1[3] | Oee1 | Oee1 | moderate | good | normal for Oee1 |
| — | Rbcs | Rbcs | Oee1 | high | high | folds greater than Oee1 alone |
| — | Rbcs | Rbcs/Oee1 | Oee1 | high | high | folds greater than Oee1 alone |
| — | Com44[4] | Com44 | Com44 | low | low | normal for Com44 |
| — | Rbcs | Com44 | Com44 | high | low | normal for Com44 |
| — | Rbcs | Rbcs/Com44 | Com44 | high | high | good import |
| — | Rbcs | Rbcs | Com44 | high | high | good import |
| — | Com70[5] | Com70 | Com70 | low | normal | normal for Com70 |
| — | Rbcs | Com70 | Com70 | high | normal | normal for Com70 |
| — | PetA[6] | PetA | PetA | low | low | normal for PetA |
| — | Rbcs | Rbcs | PetA | high | high | high |
| — | Rbcs | — | PetA | high | low | none due to loss of signal |
| — | Rbcs | Rbcs/PetA | PetA | high | high | high |
| — | Oee1 | Oee1 | Dhfr[7] | moderate | good | a foreign protein |
| — | Dhfr | — | Dhfr | low | no | lacks transit signal |
| — | Rbcs | Rbcs | Dhfr | high | high | high |
| — | Rbcs | Rbcs | Pka[8] | high | high | higher than Pka itself |
| — | Rbcs | Rbcs | Pkg[9] | high | high | higher than Pkg itself |
| — | Pka | Pka | Pka | moderate | good | normal for Pka |
| — | Pkg | Pkg | Pkg | moderate | good | normal levels for Pka |
| — | Pkg | Pkg | Rbcs | moderate | good | resembles Pkg levels |

[1]pea
[2]pea
[3]*Arabidopsis thaliana*
[4]*Brassica napus*
[5]*Spinacea oleracea* (spinach)
[6]*Vicia faba*
[7]mouse
[8]*Ricinus cummunis* (castor)
[9]*Nicotiana tabacum* (tobacco)

Example 2
Construction of Rbcs-Cab Gene Construct

To produce transgenic tobacco plants with enhanced low light photosynthetic capacity through elevation of type I LhcIIb Cab protein levels, an enhancement of transcription, mRNA stability, translation and protein import was attained. The coding portion of the gene construct was a fusion of a DNA sequence (FIG. 1, SEQ ID NO:1) encoding the mature portion of the type I LhcIIb Cab protein (FIG. 1, SEQ ID NO:2) from pea. The coding sequence for native transit peptide was removed and replaced with a sequence for the transit peptide from the pea small subunit of Rbc (A. R. Cashmore, in *Genetic Engineering of Plants*, T. Kosugi, C. P. Meredith, A. Hollaender, Eds. (Plenum Press, New York, 1983) pp. 29–38). The 5' and 3' ends of the type I LhcIIb cab gene sequence used in the present construct are shown in FIG. 1. The Rbcs transit peptide (SEQ ID NO:4), and corresponding gene sequence (SEQ ID NO:3), are shown in Table 3, together with a short linker sequence linking the transit peptide to the Cab peptide. A 29 base pair 5' untranslated DNA sequence (5'UTR) originating immediately upstream of the pea Rbcs transit peptide coding region was used as a translation enhancer. This sequence is shown in Table 3 and is included within SEQ ID NO: 3 (nucleotides 1 to 29). Expression of the gene construct was facilitated by the strong CaMV 35S promoter (Odell, J. T. et al. (1985)

Nature 313:810) and transcriptional termination signals originated from the pea Cab gene (A. R. Cashmore (1984) Proc. Natl. Acad. Sci. USA 81:2960. A summary of the gene construct is shown in Table 3.

TABLE 3

Summary of the 35SCAMV-Rbcs-Cab Gene Construct

Key structural parts:

Rbcs (5 untranslated sequence)-pea Rbcs transit peptide-pea Cab protein body

Published genetic names of key parts:

SS3.6 (5'untranslated sequence)-SS3.6 Rbcs transit peptide-AB80 Cab protein body Sequence of key parts:

```
ACGTTGCAATTCATACAGAAGTGAGAAAA ATG GCT TCT ATG ATA TCC
                              M   A   S   M   I   S

TCT TCC GCT GTG ACA ACA GTC AGC CGT GCC TCT AGG GGG CAA TCC GCC
 S   S   A   V   T   T   V   S   R   A   S   R   G   N   S   A

GCA GTG GCT CCA TTC GGC GGC CTC AAA TCC ATG ACT GGA TTC CCA GTG
 A   V   A   P   F   G   G   L   K   S   M   T   G   F   P   V

AAG AAG GTC AAC ACT GAC ATT ACT TCC ATT ACA GAC AAT GGT GGA
 K   K   V   Q   T   E   I   T   S   I   T   S   Q   G   G

AGA GTA AAG TGC ATG GAT CCT GTA GAG AAG TCT..... (SEQ ID NO:3)
 R   V   K   C   M   D   P   L   E   K   S (SEQ ID NO:4)
           Rbcs ←                → Cab
```

Promoter:

35S CaMV

Terminator:

Cab termination sequences (Cashmore (1984) Proc. Nat. Acad. Sci. USA 81:2960–2964)

Binary vector:

EcoRI-PvuII CAMV-Rbcs-Cab into BamHI/blunt end site of pEND4K (kanamycin resistance) Klee et al. (1985) Biotechnology 3:637–642).

Agrobacterium strain:

LBA4404

Agrobacterium transformation:

Freeze-thaw method (Holsters et al. (1978) Mol. Gen. Genet. 163:181–187)

Transformation protocol:

Leaf disc procedure (Horsh et al. (1985) Science 227:1229–1231)

Cloning was initiated by the construction of the pSSTP vector containing a DNA sequence encoding the Rbcs 5'UTR and transit peptide (FIG. 2). The DNA fragment containing the required components was retrieved from plasmid pSSNPT (A. R. Cashmore, Univ. Pennsylvania, Philadelphia, Pa.) by digestion with HindIII. Phenol and chloroform:isoamyl alcohol extraction and ethanol precipitation in the presence of 0.1 M NaCl followed by a 70% ethanol wash were applied after each step of DNA manipulation as described in Example 1 to inactivate enzymes and to concentrate the DNA. The DNA precipitate was collected by centrifugation, dried and redissolved in 10 μl water. The HindIII end was rendered blunt utilizing the Klenow fragment of E. coli DNA polymerase I (Promega). The reaction consisted of 1 unit of Klenow, 0.1 mM each of dATP, dCTP, dGTP and dTTP, 50 mM Tris-HCl pH7.5, 10 mM MgCl$_2$, 5 mM DTT, and the DNA from the above step, and was incubated at 37° C. for 1 h. After repurification by organic solvent extractions, the DNA was digested with BamHI, separating the required DNA fragment from the rest of the PSSNPT plasmid. The HindIII-BamHI DNA fragment was gel purified and ligated into the SmaI and BamHI sites of pGEM4 (Promega) that had been cleaved and subsequently dephosphorylated by calf intestinal alkaline phosphatase (Pharmacia). The purification of DNA was carried out using the standard low melting agarose gel and phenol extraction method (Sambrook et al. 1989, supra.). The low melting agarose was purchased from BRL (Gaithersburg, Md., USA). DNA was recovered from appropriate low melting agarose slices by heating at 65° C. followed by extraction with phenol, prewarmed initially at 37° C., and centrifugation. The phenol extraction was repeated and the aqueous DNA layer was then adjusted to 0.1 M NaCl and centrifuged for 10 min in a microfuge. The supernatant was subjected to chloroform:isoamyl alcohol extraction followed by precipitation in ethanol as described above. The DNA pellet was collected by centrifugation, washed with 70% ethanol, dried and resuspended in water.

Figure 3:
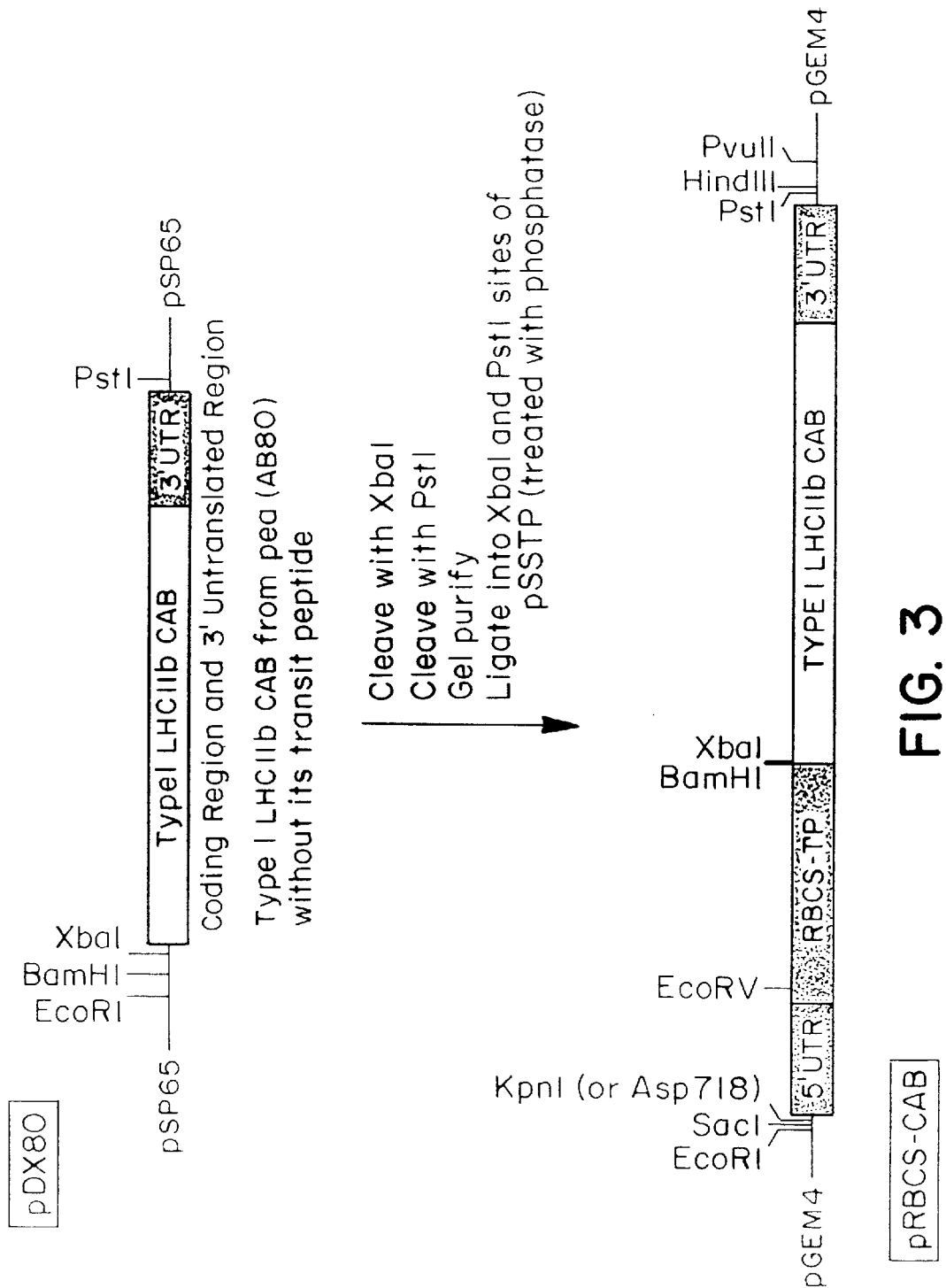
FIG. 3 shows the construction of vector pRBCS-CAB.

The mature type I LhcIIb Cab coding DNA sequence (pea AB80), contained in a XbaI-PstI DNA fragment, was retrieved by digesting plasmid pDX80 (A. R. Cashmore, Univ. Pennsylvania, Philadelphia, Pa.) with XbaI and PstI (FIG. 3). The DNA fragment was also gel purified and inserted into the plasmid vector pSSTP (FIG. 2) via the XbaI and PstI sites. Prior to ligation, these sites had been dephosphorylated by adjusting the restriction digestion reaction with 3.5 µl 1M Tris-HCl, pH 8.0 and adding 0.5 units of calf intestinal alkaline phosphatase. Following a minute incubation at 37° C., the dephosphorylated vector was repurified by organic solvent extraction and precipitated with ethanol. The resulting plasmid was designated PRBCS-CAB (FIG. 3).

Figure 4:
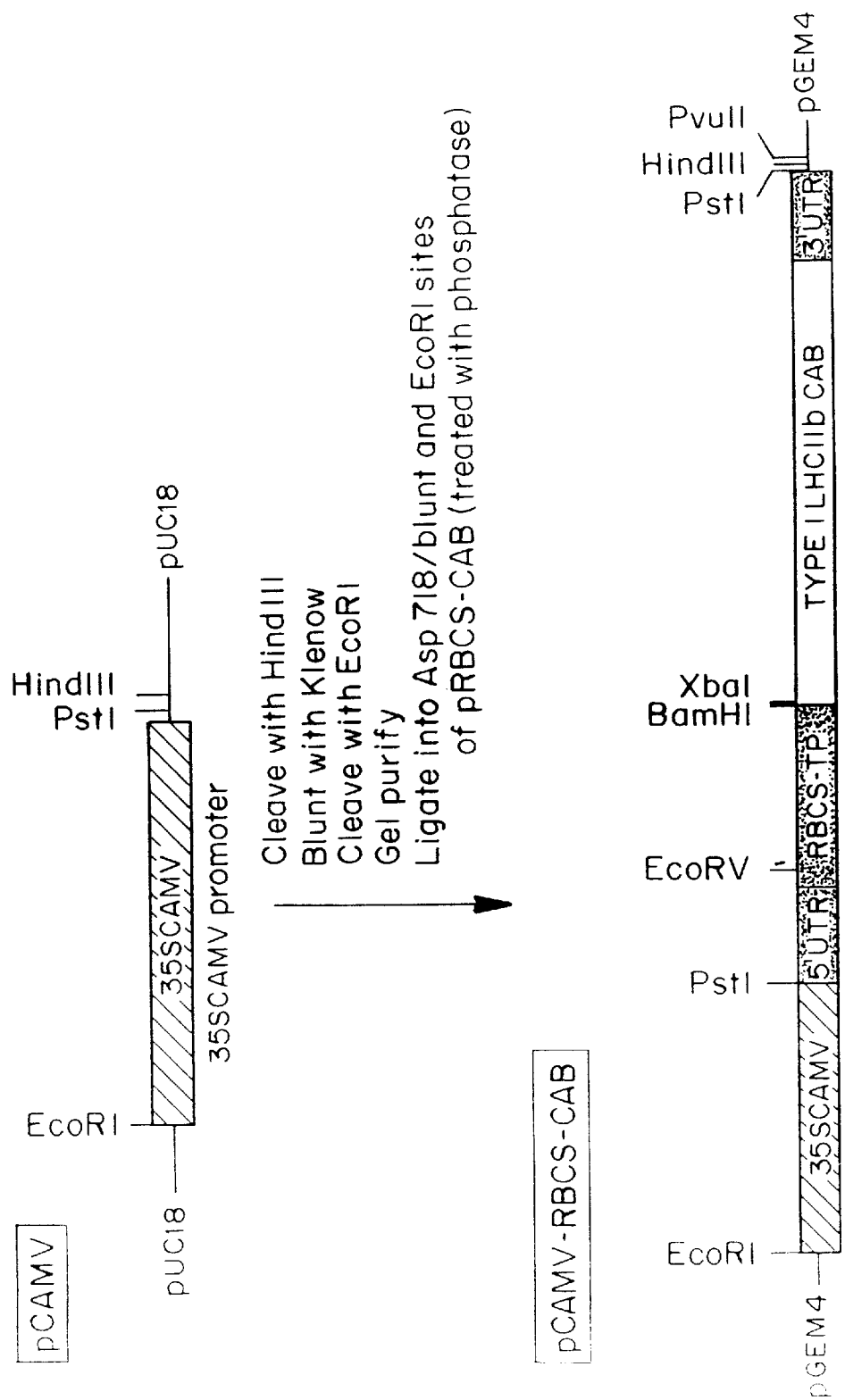
FIG. 4 shows the construction of vector pCAMV-RBCS-CAB.
Figure 5:
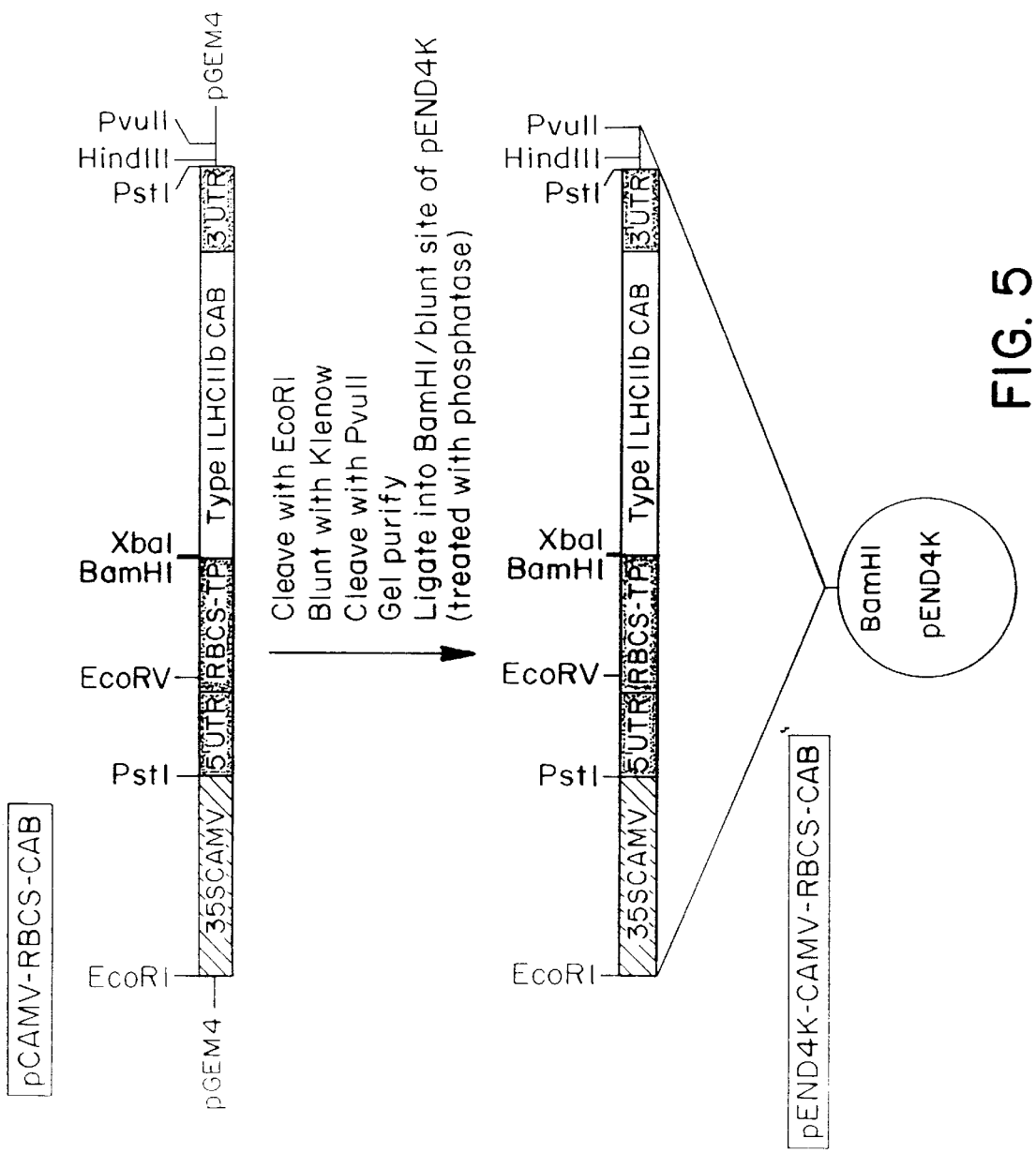
FIG. 5 shows the construction of Agrobacterium binary vector (pEND4K-CAMV-RBCS-CAB).
Figure 6:
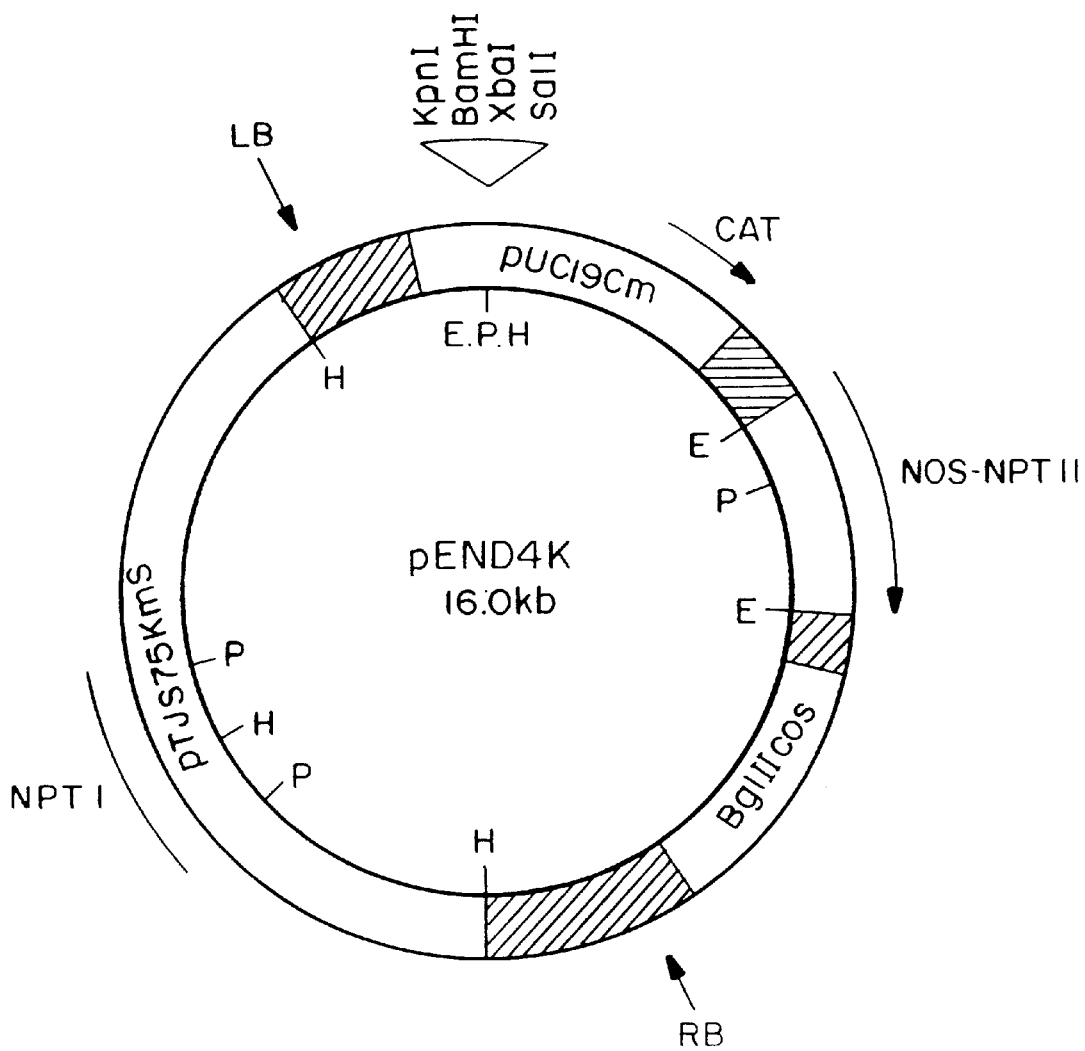
FIG. 6 is a restriction map of Agrobacterium binary vector pEND4K.

The Rbcs-Cab chimeric gene was fused to the 35S CaMV constitutive promoter by inserting a gel-purified EcoRI-HindIII fragment carrying the 35S CaMV promoter from plasmid pCAMV (A. R. Cashmore, Univ. Pennsylvania, Philadelphia, Pa.) into the EcoRI-Asp718 sites of pRBCS-CAB (FIG. 4). The corresponding HindIII and Asp718 restriction sites were made blunt using the Klenow fragment of DNA polymerase I. The 35S CaMV-Rbcs-Cab construct was then transferred as an EcoRI-PvuII DNA fragment to the BamHI site of the binary vector pEND4K (FIGS. 5 and 6) (Klee, H. et al. (1985) *Biotechnology* 3:637). All of the restriction enzyme-generated ends were made blunt by Klenow fragment in this step.

All ligation steps were carried out at 15° C. overnight using T4 DNA ligase. The ligation reactions consisted of the two appropriate target DNA molecules, ligase buffer (50 mM Tris-HCl pH 7.5, 10 mM $MgCl_2$, 1 mM DTT, 1 mM ATP) and 1–3 units of enzyme. All appropriate steps of the gene construction process were introduced into bacteria using standard $CaCl_2$ bacterial transformation protocol (Sambrook et al. 1989, supra) and the *E. coli* host strain HB101. All recombinant plasmids were propagated in HB101 and isolated using standard techniques (Sambrook et al. 1989, supra). The resolution of DNA fragments was facilitated by using standard agarose and polyacrylamide gel electrophoresis techniques.

Example 3
Transformation and Selection of Plants

The pEND4K-CAMV-Rbcs-Cab plasmid was introduced into Agrobacterium using the freeze-thaw method (Holsters et al. (1978) *Mol. Gen. Genet.* 163:181–187). Competent LBA4404 cells were obtained by inoculating 50 ml of LB broth (50 µg/ml rifampicin) with 500 µL of an overnight culture, followed by incubation at 28° C. with vigorous shaking until the cell density measured $0.7_{OD}$ at 650 nm. Cells were harvested by centrifugation at 2000×g for 5 min at 4° C., washed in ice cold 0.1M $CaCl_2$ and resuspended in 1 ml of ice cold 20 mM $CaCl_2$. A 150 µl aliquot of competent LBA4404 cells was mixed with 1 µg of plasmid DNA in a microfuge tube, and immediately frozen in liquid nitrogen. These cells were incubated at 37° C. in a water bath or thermostat block for 5 min, 1 ml of LB broth added, and the mixture incubated at 28° C. with shaking for 3 h. The cells were recovered by centrifugation at 2000×g for 5 min and resuspended in 100 µl of LB broth. Cells were plated on LB plates containing 100 µg/ml kanamycin and 50 µg/ml rifampicin and incubated for 2 days at 28° C. The presence of the pEND4K-CAMV-Rbcs-Cab plasmid was confirmed by Southern blot analysis of plasmid preparations obtained from single kanamycin-resistant colonies. Three ml of YEB broth containing 50 µg/ml rifampicin and 100 µg/ml kanamycin were inoculated with a kanamycin-resistant colony and incubated overnight at 28° C. with shaking. The overnight culture (1.5 ml) was centrifuged for 30 sec in a microfuge. The cells were resuspended in 0.1 ml of GTE solution (50 mM glucose, 10 mM $Na_2EDTA$, 25 mM Tris-HCl pH 8.0) with 4 mg/ml of lysozyme, and incubated at room temperature for 10 min. Phenol (30 µl) previously equilibrated with 2 vols of 1% (w/v) SDS, 0.2N NaOH was added. The mixture was vortexed gently until viscous and incubated at room temperature for 10 min. The lysed cells were neutralized with 3M sodium acetate, pH 4.8 (150 µl) and incubated at −20° C. for 15 min. before the mixture was centrifuged for 3 min in a microfuge. The supernatant was transferred to a fresh microfuge tube, two volumes of ethanol added, and the mixture was incubated at −80° C. for 15 min to precipitate the DNA. Following centrifugation, the DNA pellet was resuspended in 90 µl of water. Ten µl of 3M sodium acetate pH 7.0 were added, followed by an equal volume of phenol/chloroform, and the mixture was vortexed. After centrifuging for 5 min in a microfuge, the supernatant was transferred to a fresh tube and the DNA precipitated by adding 2 volumes of 100% ethanol. After centrifugation, the pellet was washed with 70% ethanol, dried and resuspended in 50 µL of TE (10 mM Tris-HCl pH 8.0, 1 mM $Na_2EDTA$).

The integrity of the pEND4K-CAMV-Rbcs-Cab plasmid in Agrobacterium was verified by restriction and Southern blot analysis of the plasmid isolated as described above and in Sambrook et al. 1989, supra. One of the Agrobacterium selected colonies containing an intact pEND4K-CAMV-Rbcs-Cab was used for plant transformation.

Tobacco plants were transformed with plasmid pEND4K-CAMV-Rbcs-Cab following the leaf disc transformation protocol essentially as described by Horsch et al. (1985) *Science* 227:1229). Only young, not fully expanded leaves, 3–7" length, from one month old plants were used. Excised leaves were surface-sterilized in 10% (v/v) sodium hypochlorite, 0.1% (v/v) Tween and rinsed 4 times with sterile deionized water. From this point on, standard aseptic techniques for the manipulation of the sterile material and media were used. Leaf discs, 6 mm in diameter, were made with the aid of a sterile paper punch and incubated for 10–20 min in a 1:5 dilution of an overnight culture of Agrobacterium harbouring the pEND4K-CaMV-Rbcs-Cab construct. After inoculation, excess bacteria were removed from the discs by briefly blotting on sterile filter paper and the discs transferred to petri dishes containing "shoot medium" (Horsch et al. (1988) in *Plant Molecular Biology Manual*, (Eds. S. B. Gelvin, R. A. Schilperoort) Kluwer Acad. Publishers, A5:1–9). Petri plates were sealed with parafilm and incubated in a growth chamber (24° C. and equipped with "grow" mixed fluorescent tubes). After two days, Agrobacterium growing on the discs were killed by washing in 500 mg/ml Cefotaxime in liquid "shoot medium" and the discs were transferred to fresh "shoot medium" containing 500 mg/ml Cefotaxime and 100 mg/ml kanamycin to select for growth of transformed tobacco cells.

Leaf discs were incubated under the same growth conditions described above for 3–5 weeks, and transferred to fresh medium on a weekly basis. During this period of time, approximately 40 green shoots emerging from the 60 discs were excised and transferred to "root medium" (Horsch et al. (1988) supra) containing 100 µg/ml kanamycin. Shoots which rooted in the presence of kanamycin and were verified to possess high levels of NptII activity (McDonnell, R. E. et al. (1987) *Plant Mol. Biol. Rep.* 5:380) were transferred to soil. Selected transformants were selfed and seeds collected. T1 seeds from seven transgenic tobacco lines displaying high levels of NptII activity were propagated at low light parameters (50–100 $\mu$mol·m$^{-2}$·s$^{-1}$) to determine which lines contained high levels of steady state transgene mRNA.

The same construct has been introduced into two cultivars of Arabidopsis, three cultivars of Brassica, tomato, lettuce and alfalfa. All of these species demonstrate increased growth in culture compared to their wild-type counterparts, especially under low light intensities. These plants have a better shade avoidance response. They grow faster, bigger and seek light more responsively than their wild-type counterparts. This is evident at 65 $\mu$moles/meter$^2$/sec of illumination in tobacco and lettuce, and 5 $\mu$mole/meter$^2$/sec of illumination for Arabidopsis.

Example 4

RNA Analysis

Figure 7A:
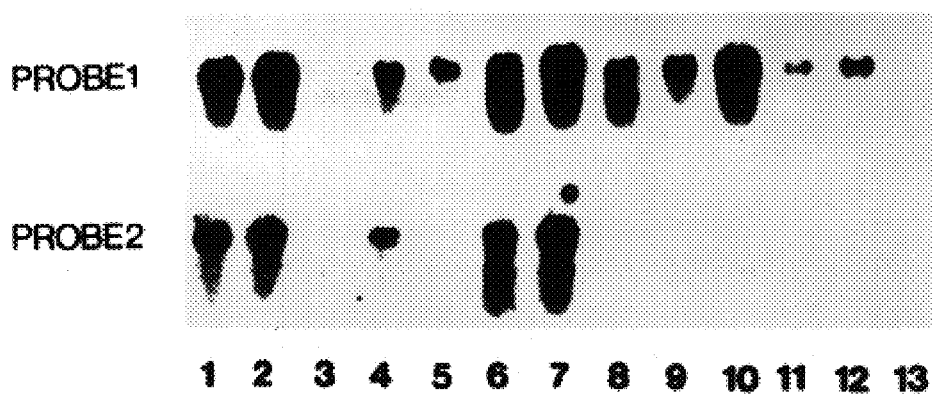
FIGS. 7A–7C show the steady state transgene transcript levels in transformed and wild-type tobacco plants.

Isolation of total RNA and subsequent blot hybridization analyses were carried out as described in A. R. Cashmore, 1982 in *Methods in Chloroplast Molecular Biology*, M. Edelman, R. B. Hallick, N. H. Chua, Eds. (Elsevier Biomedical Press, pp. 533–542) and Maniatis, T., Fritsch, E. F., and Sambrook, J., *Molecular Cloning: A Laboratory Manual*, (Cold Spring Harbor Laboratory, Cold Spring Harbor, N.Y., 1982)). Total RNA was isolated from twenty individual T1 plants from each primary transformant. Leaf samples were collected between 11:00 a.m. and 1:00 p.m. Formaldehyde denaturing gels were used to resolve RNA and transferred onto nitrocellulose as described (Sambrook et al. 1989, supra). The RNA blot (FIG. 7A) was probed with the pea Cab DNA probe (marked PROBE 1), stripped and rehybridized with the pea Rbcs transit peptide-specific DNA probe (marked PROBE 2). Numbers 1–7 indicate the primary transformants carrying the Rbcs-Cab transgene and exhibiting high levels of NptII activity. Plants 7–12 represent plants that have been transformed with a control pea Cab construct. Plant 13 represents a wild-type nontransformed tobacco plant (*Nicotiana tabacum* cv. Petit Havana SR1). Transcript levels detected by the pea Cab DNA probe were normalized and quantitated by laser densitometry. Plants arising from transformant lines 3 and contained the lowest amount of pea cab mRNA, whereas lines 1, 2 and 7 contained the highest levels. The same results were obtained with the pea Rbcs transit peptide-specific DNA probe (FIG. 7A). Total RNA from wild-type plants (WT) did not hybridize to either of the DNA probes.

Figure 7B:
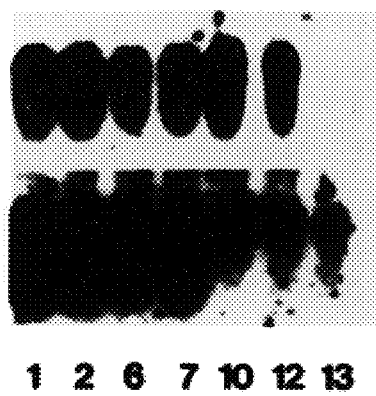

Individual T1 plants from the lines with the highest observed transgene mRNA levels were self-crossed and subjected to segregation analysis. The transgene mRNA levels of subsequent homozygous lines were analyzed in the same manner as the primary transformant lines (FIG. 7B). Numbers indicate the derivation of the homozygous lines. Seeds were germinated at 24° C. on moist filter paper, transferred to pots containing a mixture of soil and vermiculite (1:1) and propagated in growth chambers set at 50–100 $\mu$mol·m$^{-2}$·s$^{-1}$ lighting with a 14 h light/10 h dark photoperiod and 24/18° C. day/night temperature. The pots were watered daily with a complete nutrient solution containing 10 mM nitrate and 2 mM ammonium. Several subsequent homozygous lines exhibited high levels of transgene mRNA and displayed the same phenotype.

Example 5

Protein and Chlorophyll Analysis

Figure 7C:
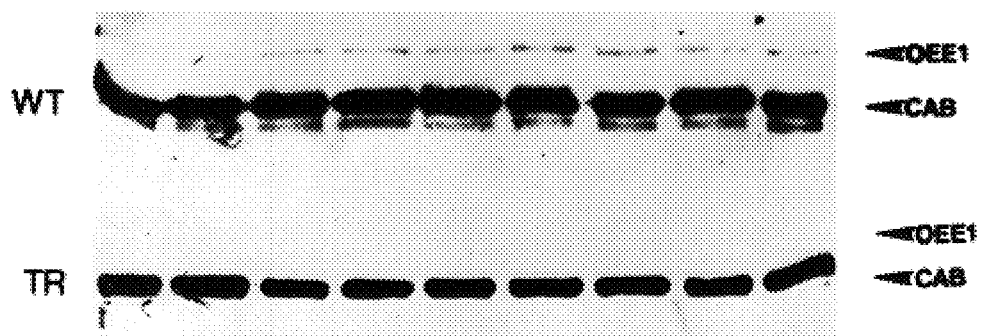

Thylakoid protein profiles of homozygous lines derived from transgenic line 2 (TR) were compared to wild-type (WT) to determine if additional transgene transcripts translated into an overall increase in steady state Cab levels. Nine different leaf disc samples were collected from homozygous transgenic lines derived from primary transformant 2 (marked TR) and from wild-type plants (marked WT). Samples were collected between 11:00 a.m. and 1:00 p.m. Thylakoids were isolated (K. E. Steinback, et al., in *Methods in Chloroplast Molecular Biology*, M. Edelman, R. B. Hallick, N. H. Chua, Eds. (Elsevier Biomedical Press, Amsterdam, 1982) pp. 863–872; Vernon, L. P. (1960) *Anal. Chem.* 32:1144) and analyzed using standard immunoblotting techniques. Cab/oeel ratios were determined by laser densitometry of the corresponding immunostained bands. The bands corresponding to Oee1 and Cab are marked. Increases in overall Cab protein levels were detected by simultaneously probing the blots with antibodies against the 33 kDa protein of the PSII oxygen-evolving complex (Oee1) and Cab (FIG. 7C). The ratio of Cab to Oee1 was used to determine Cab levels relative to PSII units by using Oee1 as an internal marker of PSII levels. The densitometry results indicated that the level of Cab protein is enhanced 2–3× relative to Oee1, suggesting that there is more Cab protein per PSII. Parallel enhancement of chlorophyll content was evident when the LhcII complexes were isolated (K. E. Steinback, (1982) supra; L. P. Vernon (1960) supra). Approximately 1.5× more chlorophyll and about 2–3× more LhcII complexes were recovered per gram of fresh weight leaf, indicating that the additional Cab proteins are functionally binding chlorophyll.

Example 6

Morphological and Developmental Analysis

Figure 8A:
FIGS. 8A–8C show the growth and morphological characteristics (FIG. 8A) of WT and TR tobacco plants (left and right, respectively). The respective 7th fully developed leaves from WT and TR are compared as diagrams of whole leaves (FIG. 8B) and transverse sections (FIG. 8C).

The TR plants, both primary transformants and subsequent selfed homozygous lines, exhibit growth and morphological differences relative to WT under all conditions tested, e.g., greenhouse or growth chambers. All plants shown were at the same developmental age and were propagated as described above. The TR plants display a higher level of vigor under low light regimes (50–80 $\mu$mol·m$^{-2}$·s$^{-1}$) (FIG. 8A).

The high light responses of the TR plants are enhanced. They produce more biomass and more robust growth patterns, depending on the intensity of the lighting conditions during propagation. The TR plants are bigger than their WT counterparts under high light intensities, such as in greenhouses. Among other characteristics, TR plants, compared to WT plants show increased stem girth and less variability in growth pattern. Further, field trials show that TR plants grow as well as WT plants in full sunlight field conditions in terms of biomass and size. No detrimental effects were observed in TR plants under these conditions.

Figure 8B:
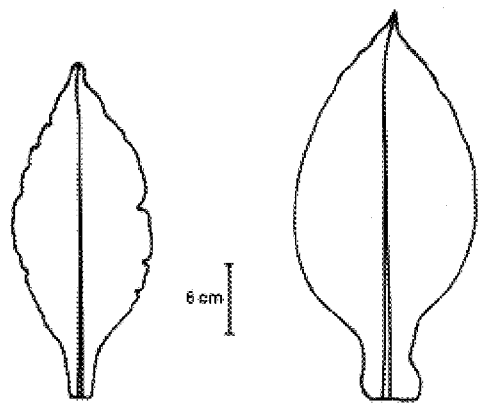
Figure 8C:
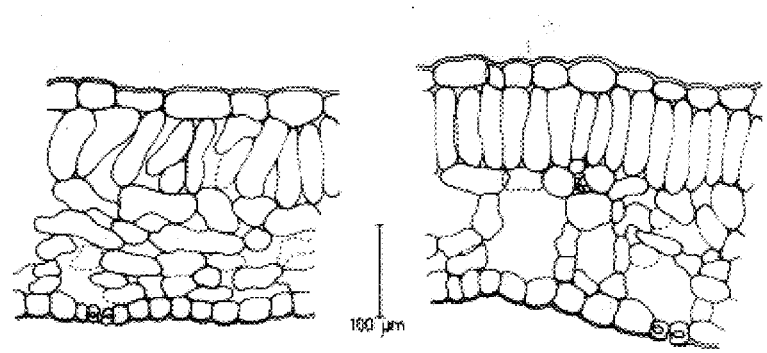

The elevation of Cab appears to induce a series of changes, the most prominent ones being broader leaves with a smooth blade, a continuous edge around the leaves, higher vegetative biomass and delayed flowering time. In addition to the overall enlargement of leaf size, the base of the petiole is more expanded relative to the WT leaves (the 7th fully developed leaf from both WT and TR were compared) (FIG. 8B). The TR leaves are thicker with relatively larger intercellular spaces (FIG. 8C). The light micrographs (FIG. 8C) represent samples from the intermediary area of the leaf blade. Leaf pieces were fixed in FAA50 and examined using a light microscope (D. A. Johansen, *Plant Microtechnique*, (McGraw-Hill Book Co., New York, 1940)).

Leaf samples were selected as above and processed for electron microscopy by fixing in 2.5% glutaraldehyde buffered with 0.1M phosphate buffer (pH 7.5) and post-fixing with 1% osmium tetroxide for 2 h. Following dehydration in an ethanol series, the leaf samples were embedded in Spurr resin, sectioned and further stained in uranyl acetate and plumb citrate (Spurr, A. R. (1969) *J. Ultrastr. Res.* 26:31; Reynolds, E. S. (1963) *J. Cell Biol.* 17:208; Watson, M. L. (1958) *J. Biophys. Biochem. Cytol.* 4:475). The same scale in the applies to both WT and TR mesophyll tissue photographs. The TR leaf cells contain higher numbers of chloroplasts on a per cell basis and the plastids are larger with a strikingly rounder shape (FIGS. 11A–D). Differences in the internal organization of the plastids, e.g. stacking of the thylakoids, were not detected at the level of resolution used. Differences were not detected at any level with respect to the mitochondria, vacuole or nucleus.

Figure 9:
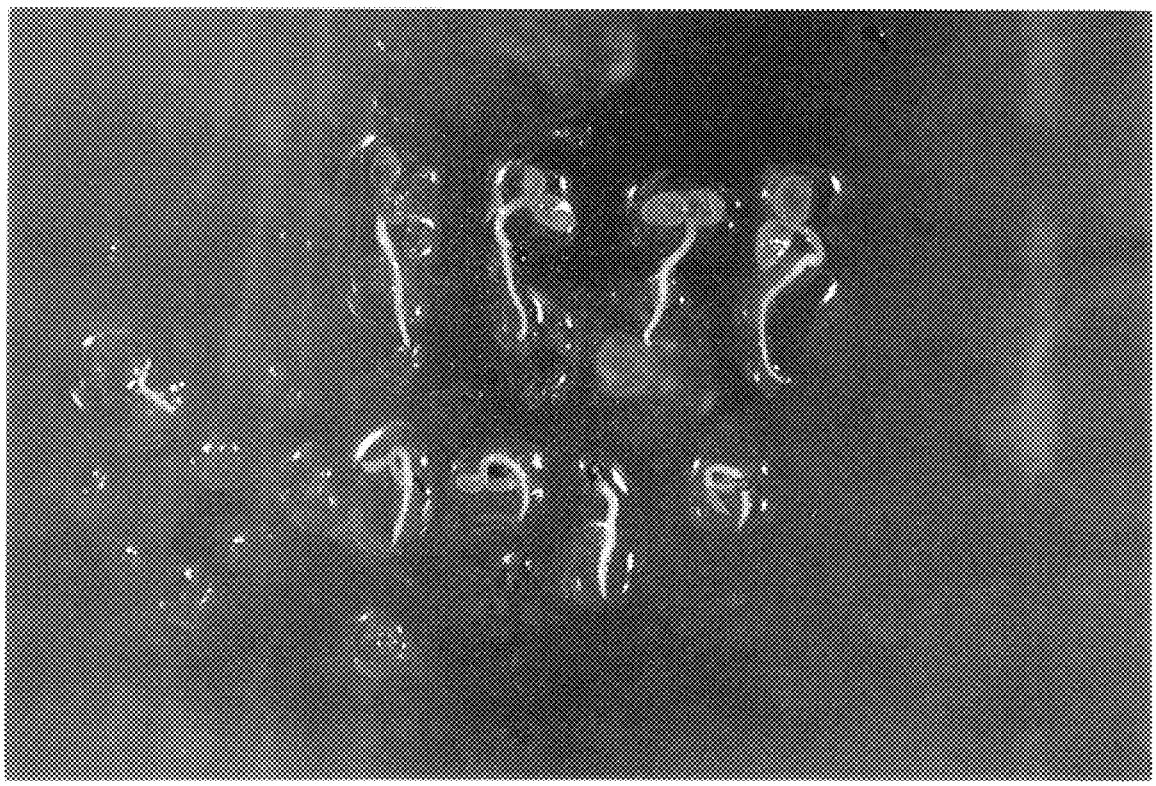
FIG. 9 is a comparison of transgenic seedlings (top row) and control seedlings (bottom row) after four days germination on solid MS media.
Figure 10A:
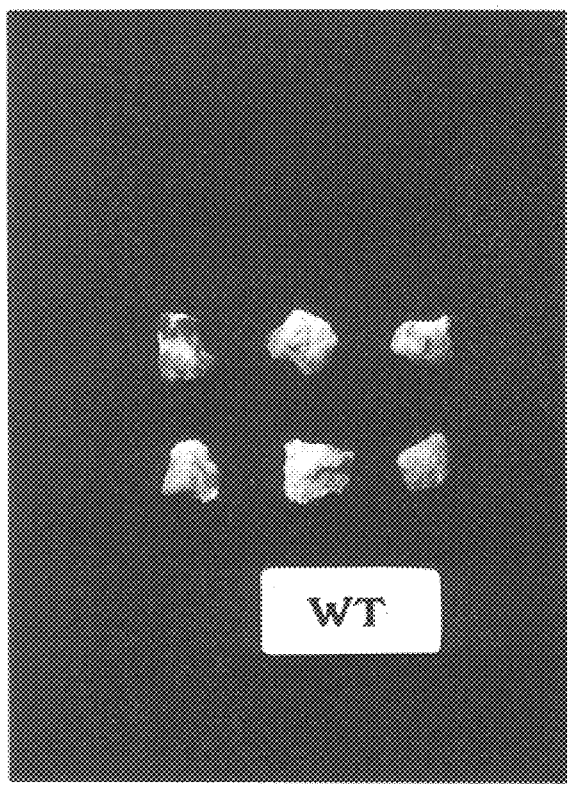
FIGS. 10A–B show a comparison of transgenic (TRA) and control (WT) tobacco callus grown for the same period of time.
Figure 10B:
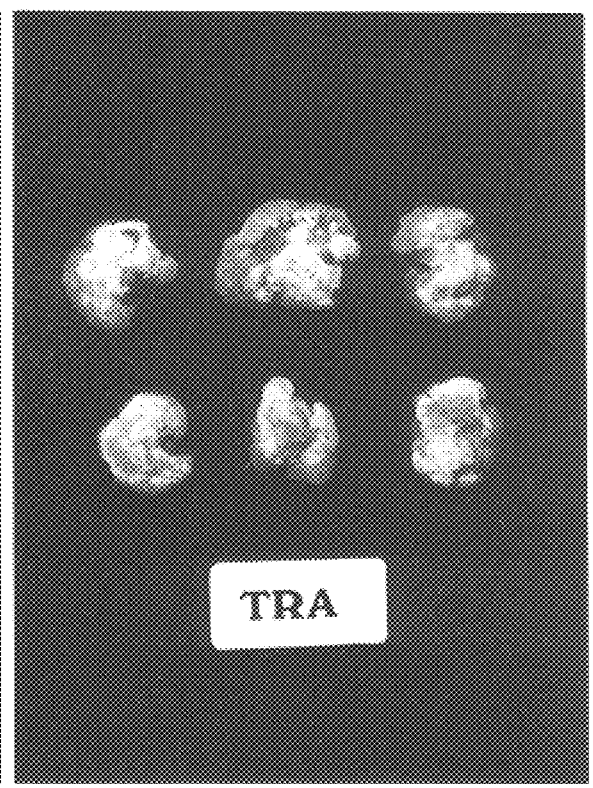
Figure 11A:
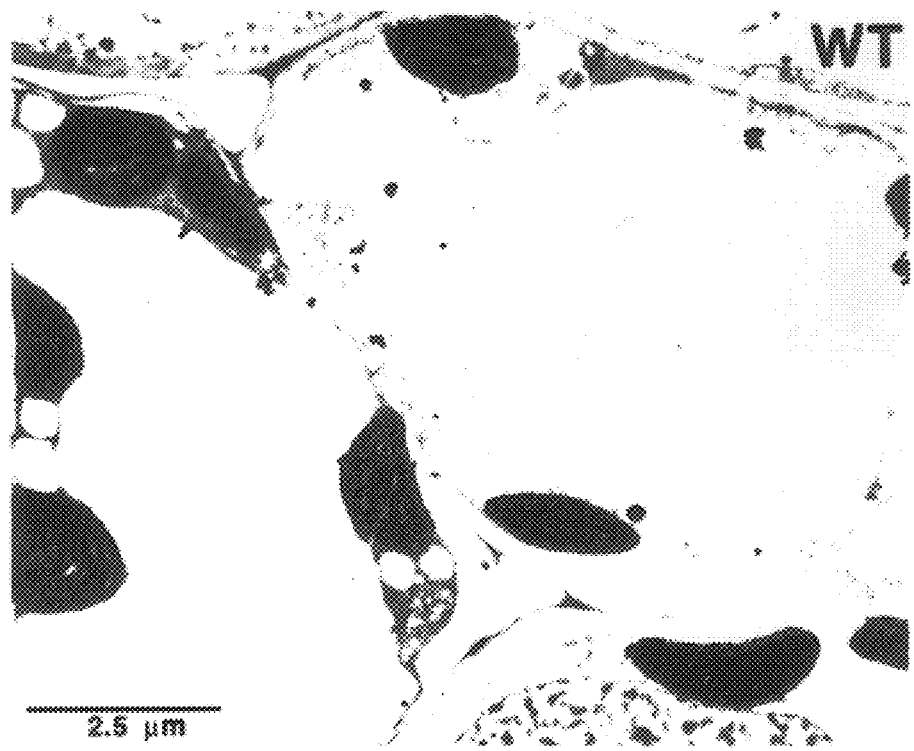
FIGS. 11A–11D show electron micrographs of wild-type (WT) and transgenic (TR) mesophyll tissues (FIGS. 11A and 11C) and chloroplasts (FIGS. 11B and 11D) of tobacco leaves.
Figure 11B:
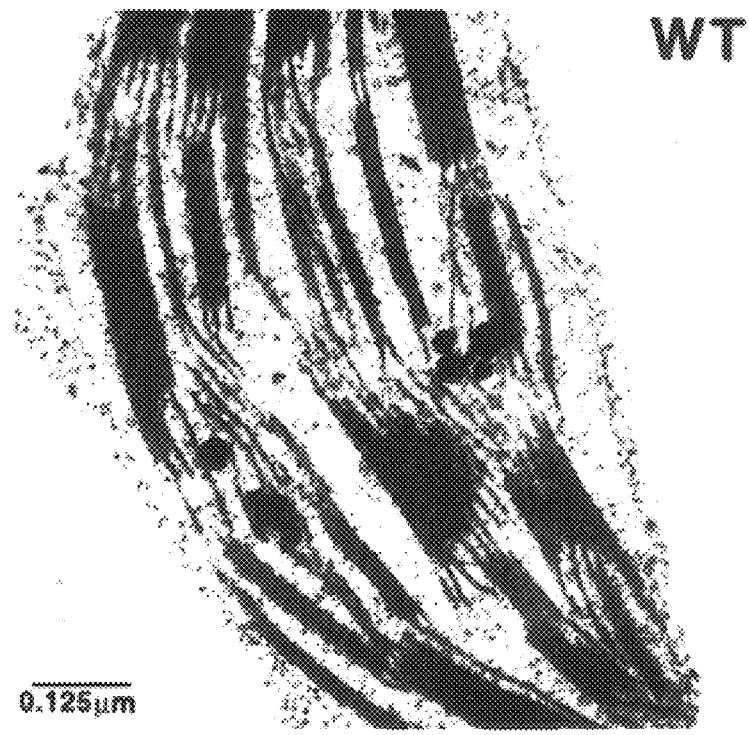
Figure 11C:
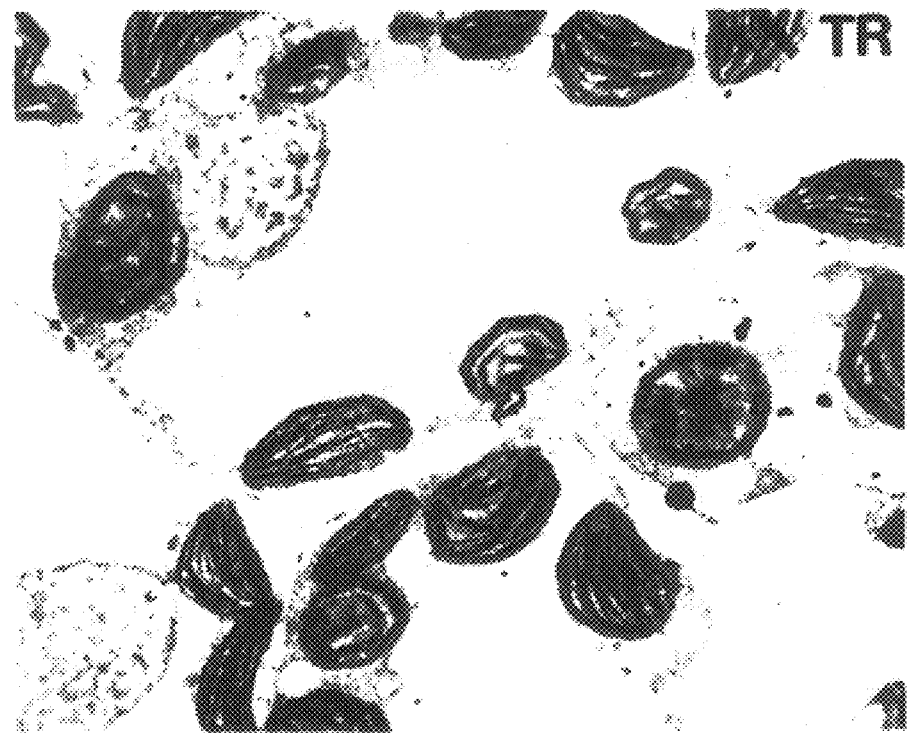
Figure 11D:
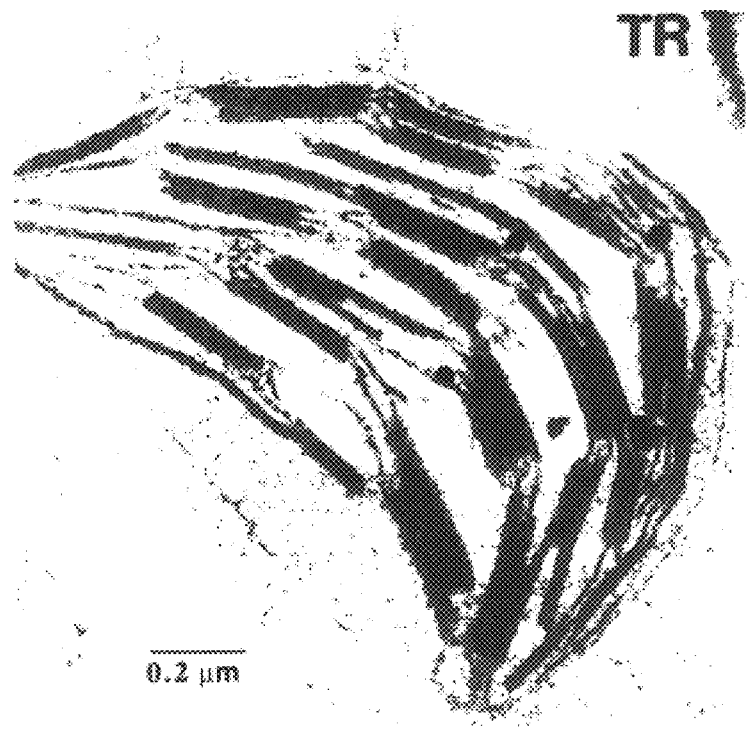

The germination rate of TR seeds was strikingly different than that of WT seeds. TR seeds germinate on average 1–3 days earlier than WT seeds on solid MS media (FIG. 9), and the newly emerged TR seedlings are already green and grow faster upon emergence than WT. The WT seedlings emerge yellowish and begin greening within the day. Callus tissue comprising TR cells grows 2–3× faster than callus comprising WT cells (FIGS. 10A–B).

Transplants of TR plants also withstand transplant shock better than transplants of WT plants. They recover and establish normal growing patterns more rapidly.

Example 7
Physiological and Biochemical Analysis

Functionality and enhancement of photosynthetic activity as a result of the extra Cab protein was assessed using four different criteria:

1) Gas exchange characteristics;
2) Metabolite level changes;
3) Carbohydrate content; and
4) PSII electron transport efficiency.

Photosynthetic rates of TR and WT plants propagated under limiting light conditions were compared. Plants were cultivated under two different light intensities, 50 $\mu mol \cdot m^{-2} \cdot s^{-1}$ (referred to as low, (FIG. 12A) and 500 $\mu mol \cdot m^{-2} \cdot s^{-1}$ (referred to as high, (FIG. 12B). Photosynthesis was measured using a leaf disc oxygen electrode (LD2/2 Hansatech, UK) under saturating 5% $CO_2$ at 25° C. The 5% $CO_2$ was supplied from 200 $\mu l$ of a 2M $KHCO_3/K_2CO_3$ mixture (pH 9.3) on felt in the base of the leaf disc electrode (Walker, D. A. (1987) *The use of the oxygen electrode and fluorescence probes in simple measurements of photosynthesis* University of Sheffield, Sheffield, U. K.). Illumination was provided by a slide projector Novomat 515 AF (Braun, Germany). The data are means of 5 plants of each phenotype. Standard deviations were less than 10% of the means.

Photosynthetic response curves of TR plants display a behavior distinct from WT plants (FIG. 12A). In low light (between 20–100 $\mu mol \cdot m^{-2} \cdot s^{-1}$), the TR plants exhibit a higher rate of photosynthesis than in WT plants; whereas, the reverse situation occurs in higher light intensities (FIG. 12A). As the light intensity increases, the response curves become more similar, intersecting at approximately 300 $\mu mol \cdot m^{-2} \cdot s^{-1}$, where TR tissue reaches saturation at a lower rate. At the same light intensity, the increase in photosynthesis is higher and has not reached saturation in WT tissue. Saturation in WT tissue occurs at about 450 $\mu mol \cdot m^{-2} \cdot s^{-1}$.

The same response was displayed by plants grown in higher irradiance (500 $\mu mol \cdot m^{-2} \cdot s^{-1}$) (FIG. 12B). The rate in TR tissue is higher than WT tissue in the range of 20–500 $\mu mol \cdot m^{-2} \cdot s^{-1}$, reaching saturation in higher light intensities, while WT remains unsaturated at 1000 $\mu mol \cdot m^{-2} \cdot s^{-1}$. The increased low light photosynthetic capacity of TR tissue was also evident in air $CO_2$ levels and at a light intensity of 100 $\mu mol \cdot m^{-2} \cdot s^{-1}$, where TR tissue exhibited an average photosynthetic rate 50% higher than WT tissue (3.3±0.8 vs. 2.2±0.8 $\mu mol\ O_2 \cdot m^{-2} \cdot s^{1}$, respectively).

Alterations in metabolite and adenylate levels are also indicators of changes in photosynthetic capacity. In low light, photosynthesis is mainly limited by the capacity of electron transport to generate ATP and NADPH, the assimilatory force FA (Heber, U. et al. (1986) *Biochim. Biophys. Acta* 852:144; Heber et al., in *Progress in Photosynthesis Research*, J. Biggins, Ed., (Martinus Nijhoff, Dordrecht) Vol. 3 (1987) pp. 293–299). The strength of $F_A$ can be estimated by the ratio of PGA (3-phosphoglyceric acid) to TP (triose phosphate) (Dietz, K. J. and Heber, U. (1984) *Biochim. Biophys. Acta.* 767:432); ibid 848:392 (1986)). Measurements were obtained under 100 and 1000 $\mu mol \cdot m^{-2} \cdot s^{-1}$ lighting, and in 850 $\mu bar$ external $CO_2$ concentration to minimize the effects of photorespiration (Table 4). When photosynthesis achieved steady state, the leaves were freeze-clamped and prepared for metabolite extraction. The $CO_2$ assimilation rate of TR leaves in 100 $\mu mol \cdot m^{-2} \cdot s^{-1}$ lighting was 53% higher than WT leaves. The levels of PGA were similar between TR and WT plants, however, the TP level was 33% higher in TR. Thus, the PGA/TP ratio is higher in WT plants, indicating a limitation in the reduction of PGA to TP by the supply of ATP and NADPH in WT plants. The changes in adenylates indicate that the ATP content in TR leaves was twice the value observed in WT leaves, whereas the ADP content in both plants was similar. The ATP/ADP ratio in the chloroplast is lower than in the cytosol, typically calculated to be between 1.5 and 3.0 (Stitt, M. et al. (1982) *Plant Physiol.* 70:971; Giersch, C. et al. (1980) *Biochim. Biophys. Acta* 590:59; Neuhaus, N. E. and Stitt, M. (1989) *Planta* 179:51). As light intensity increases, the ratio decreases even further (Dietz and Heber, supra ). The ATP/ADP ratio is higher in TR plants than WT plants (2.2 vs. 0.8). These results indicate that TR plants have an increased capacity to generate ATP in low light, leading to an enhancement of PGA reduction and a higher photosynthetic rate.

Changes in the level of hexose phosphate were also observed, with more hexose phosphate in WT than TR plants. The G6P/F6P ratio is an indicator of hexose distribution in a cell, with values of 1–2 indicating chloroplastic compartmentalization and predominantly starch synthesis, and ratios of 3–5 indicating a cytoplasmic location with sucrose synthesis being dominant (Gerhardt, R. et al. (1987) *Plant Physiol.* 83:399). Thus, the low G6P/F6P values for both WT and TR plants grown in low light indicate that the carbon fixed is being partitioned mainly into starch.

The enhanced capacity to absorb light has a negative effect on photosynthetic metabolism of TR plants in high irradiance regimes. The photosynthetic rate of WT plants was instead 37% higher than that of TR plants. The changes in metabolite levels and ratios indicate that major alterations in the regulatory mechanisms of photosynthesis have occurred in TR plants to compensate for the enhanced light-absorbing capacity in high light. The PGA/TP ratio was identical in both plants and the ATP/ADP ratio was lower in TR plants indicating that photophosphorylation was limiting photosynthesis. The change in partitioning indicated by the G6P/F6P ratio increase (2.9 vs. 3.9 in WT and TR plants, respectively) points to an increase in sucrose synthesis to compensate for the elevated demand for inorganic phosphate (Pi) in TR plants. The TR plants appear to be less efficient in the recycling of Pi via sucrose synthesis in high light.

TABLE 4

Photosynthesis and metabolite content in plants grown under 50 $\mu$mol · m$^{-2}$ · s$^{-1}$ lighting

| Plant Type | CER ($\mu$mol · m$^{-2}$ · s$^{-1}$) | 100 $\mu$mol · m$^{-2}$ · s$^{-1}$ Metabolite Content (nmol · mg$^{-1}$ Chl.) | | | | | | | Metabolite Ratio (mol/mol) | | |
|---|---|---|---|---|---|---|---|---|---|---|---|
| | | PGA | TP | ATP | ADP | G6P | F6P | G1P | PGA/TP | ATP/ADP | G6P/F6P |
| Wild-type | 1.7 ± 0.1 | 364 ± 110 | 46 ± 21 | 74 ± 27 | 89 ± 51 | 92 ± 39 | 98 ± 40 | 69 ± 48 | 8.4 | 0.8 | 0.9 |
| Transgenic | 2.6 ± 0.6 | 353 ± 47 | 61 ± 8 | 181 ± 38 | 85 ± 32 | 43 ± 9 | 65 ± 38 | 61 ± 9 | 5.8 | 2.2 | 0.7 |
| | | | | 1000 $\mu$mol · m$^{-2}$ · s$^{-1}$ | | | | | | | |
| Wild-type | 8.8 ± 0.7 | 320 ± 174 | 92 ± 49 | 112 ± 43 | 86 ± 37 | 174 ± 62 | 59 ± 7 | 40 ± 9 | 3.5 | 1.2 | 2.9 |
| Transgenic | 6.4 ± 1.8 | 259 ± 54 | 73 ± 17 | 89 ± 32 | 150 ± 49 | 217 ± 66 | 56 ± 27 | 40 ± 23 | 3.5 | 0.6 | 3.9 |

External CO$_2$ concentration was 850 $\mu$l · L − 1 and leaf temperature was 25° C.
The data presented are averages of 4 plants ± SD.
The rates of CO$_2$ assimilation were measured in an open gas exchange system using a Binos100 (Rosemount, Germany) infra-red gas analyser.
The leaf chamber was designed and built with aluminum alloy to allow rapid acquisition of leaf disc samples and quick freezing.
The lower side of the chamber was sealed with Parafilm, through which a pneumatically driven liquid N$_2$-frozen copper rod could enter.
The upper side of the chamber contained a clear acrylic ring to stop the leaf disc cutter.
The frozen leaf discs (8 cm$^2$) were stored in liquid N$_2$ until use.
Actinic illumination was provided from two branches of the fiber optic from a KL1500 cold light source (Schott, Maiz Germany) directed onto the top of the chamber at a 45° C. angle.
Chamber temperature was controlled by circulating water through the chamber cavity.
The water vapor deficit of the incoming air was readjusted to 18 mbar by passing the air stream to a coil immersed in a water bath kept at 15° C.
Leaf samples were extracted in 10% (v/v) HClO$_4$ and the indicated metabolites were determined using a Hitachi U-3300 (Tokyo, Japan) spectrophotometer (Labate, C. A. and R. C. Leegood, R. C. (1989) Plant Physiol. 91:905; Lowry, O. H. and Pasonneau, J. V. (1972) A flexible system of enzymatic analysis (Academic Press, New York).

Changes in photosynthetic activity were also reflected in carbohydrate content. Starch and sucrose contents were relatively balanced with no major partitioning changes in young leaves of TR or in WT plants under both lighting regimes (50 and 500 $\mu$mol·m$^{-2}$·s$^{-1}$) (Table 5A). Sucrose and starch were produced in equal amounts except that the total carbohydrate content in TR plants was 2–3× higher than in WT plants. The seeds of TR plants contained 2× more starch than WT seeds when grown under low light and then shifted to high light at later stages of growth. The total carbohydrate level of TR and WT plants appeared unaffected by lighting changes in the young leaves.

A similar situation occurs in fully developed WT leaves (Table 5B), with starch and sucrose levels remaining fairly balanced and largely independent of lighting. The overall carbohydrate levels, however, were higher than in young leaves. TR leaves at the same developmental stage react differently to the two lighting regimes by varying the starch and sucrose levels. Sucrose levels were higher in low light, whereas starch was greater in high irradiance. Although the total carbohydrate levels increase substantially in high light in both TR and WT leaves, the level in TR leaves was approximately 49% higher than in WT leaves.

TABLE 5

Carbohydrate content in young and fully developed leaves (A) Starch and sucrose content in young leaves.
The data are averages of 4 plants ± SD.

| Plant Type | Starch | Sucrose | Total Carbohydrate |
|---|---|---|---|
| | $\mu$mol hexoses equivalents · mg − 1Ch1 | | |
| Plants cultivated under 50 $\mu$mol · m$^{-2}$ s$^{-1}$ | | | |
| Wild-type | 0.6 ± 0.2 | 0.8 ± 0.1 | 1.4 ± 0.3 |
| Transgenic | 1.3 ± 0.2 | 1.6 ± 0.4 | 3.0 ± 0.6 |
| Plants cultivated under 500 $\mu$mol · m$^{-2}$ s$^{-1}$ | | | |
| Wild-type | 0.6 ± 0.3 | 0.4 ± 0.1 | 1.0 ± 0.4 |
| Transgenic | 1.8 ± 0.5 | 1.4 ± 0.4 | 3.2 ± 0.9 |

TABLE 5-continued

Carbohydrate content in young and fully developed leaves (B) Starch and sucrose content in fully developed leaves.
The data are averages of 6 plants ± SD.

| Plant Type | Starch | Sucrose | Total Carbohydrate |
|---|---|---|---|
| | $\mu$mol hexoses equivalents · mg − 1Ch1 | | |
| Plants cultivated under 50 $\mu$mol · m$^{-2}$ s$^{-1}$ | | | |
| Wild-type | 1.2 ± 0.4 | 1.8 ± 1.2 | 3.0 ± 1.6 |
| Transgenic | 1.2 ± 0.5 | 2.1 ± 1.4 | 3.3 ± 1.9 |
| Plants cultivated under 500 $\mu$mol · m$^{-2}$ s$^{-1}$ | | | |
| Wild-type | 4.1 ± 1.9 | 3.8 ± 1.9 | 7.9 ± 3.8 |
| Transgenic | 7.0 ± 2.8 | 4.8 ± 1.8 | 11.8 ± 4.6 |

Soluble sugars were assayed spectrophotometrically following the extraction of leaves in HClO$_4$.
For estimation of starch, the insoluble leaf extracts were washed with 0.5M MES-HCl (pH 4.5), resuspended in 0.5 ml of the same buffer, and digested with an amylase (4 units ml − 1)-amyloglucosidase (14 units ml − 1) cocktail. After centrifugation, the supernatants were assayed for glucose (Jones, M. G. K. et al. (1977) Plant Physiol. 60:379).

FIG. 13 shows the light response curves for qP (FIG. 13A), qN (FIG. 13B), Fv/Fm (FIG. 13C) and $\emptyset_{PSII}$ (FIG. 13D) measured in air for WT and TR plants grown for 6–8 weeks postgermination. The data are means of 4 plants of each phenotype. Standard deviations were less than 5% of the means. Chlorophyll fluorescence was analyzed using a pulse amplitude modulation fluorometer (PAM101, Heinz Walz, Effeltrich, Germany). Fo (base fluorescence in dark) was measured in leaves dark-adapted (for a period of 30–60 min) using a weak modulated measuring light (approximately 1 $\mu$mol·m$^{-2}$·s$^{-1}$) provided by a fibre optic probe located under the lower window of the leaf chamber (approximately 5 mm from the leaf surface), which also collected the fluorescence signal. For the determination of maximal fluorescence (Fm), a saturating pulse of light (7500 $\mu$mol·m$^{-2}$·s$^{-1}$), activated by a PAM103 trigger control unit, was applied at a frequency of 30 s and a duration of 1 s. The steady state fluorescence yield (Fs) was monitored following the onset of illumination with actinic light. The photochemical (qP) and non-photochemical (qN) quenching parameters were determined according to Schreiber et al. (1986) *Photosynth. Res.* 10:51. The quantum efficiency of electron flux through PSII $\emptyset_{PSII}$ was determined by the product of qP and the efficiency of excitation capture by open PSII reaction centers (Fv/Fm) (Genty et al. (1989) *Biochim. Biophys. Acta.* 990:87).

The effect of extra Cab protein on electron transport efficiency by PSII ($\emptyset_{PSII}$) in response to varying irradiance was determined by measuring chlorophyll fluorescence characteristics (Genty, et al. (1989) supra) in air at steady state photosynthesis (FIGS. 13A–D). Measurements were carried out with plants propagated in low irradiance (50 $\mu mol \cdot m^{-2} \cdot s^{-1}$). There was a corresponding decrease in $\emptyset_{PSII}$ as light intensity increased (FIG. 13D), with a less pronounced decline in TR plants. The quantum efficiency of open PSII reaction centers (Fv/Fm) also decreased with increasing light intensity; however, TR plants displayed a different pattern from 100 to 600 $\mu mol \cdot m^{-2} \cdot s^{-1}$ (FIG. 13C). The Fv/Fm decline in TR plants was less substantial than in WT plants between this range of light intensities, becoming more similar to WT plants above this range. The efficiency of $\emptyset_{PSII}$ can be determined by the product of Fv/Fm and the photochemical quenching of chlorophyll fluorescence (qP). The qP value reflects the oxidized state of the primary acceptor $Q_A$ (Schreiber, U. et al. (1986) supra). A decrease in qP as light intensity increased was observed (FIG. 13A). The TR plants remain significantly more oxidized than WT except at high irradiance. The chlorophyll fluorescence data also indicate that exposure of TR plants to high irradiance does not lead to photoinhibition since Fv/Fm ratios were similar for TR and WT plants.

Figure 13B:
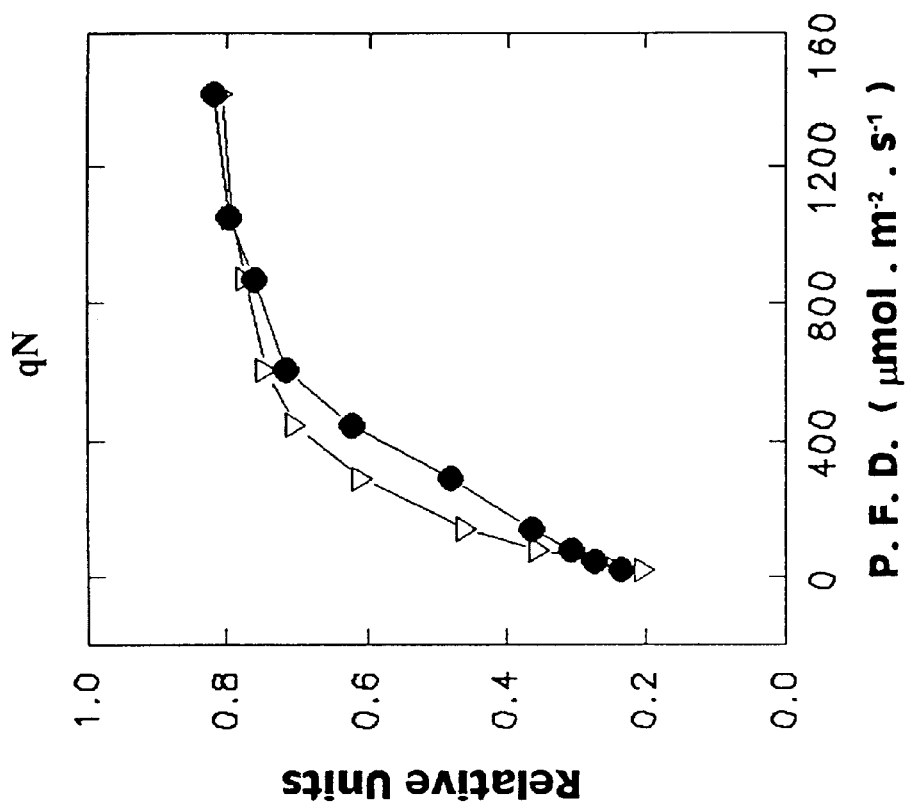
FIGS. 13A–13D show the light response curves for qP (FIG. 13A), qN (FIG. 13B), Fv/Fm (FIG. 13C), and $\emptyset O_{PSII}$ (FIG. 13D) measured in air for WT($\nabla$) and TR($\bullet$) plants.
Figure 13A:
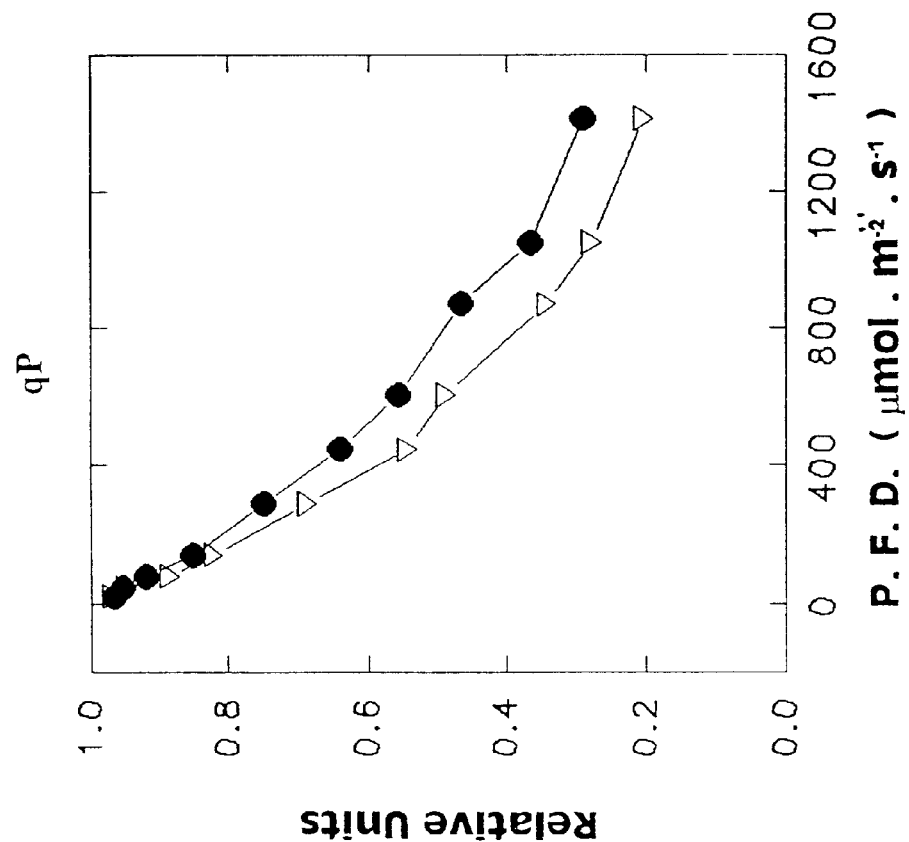
Figure 13D:
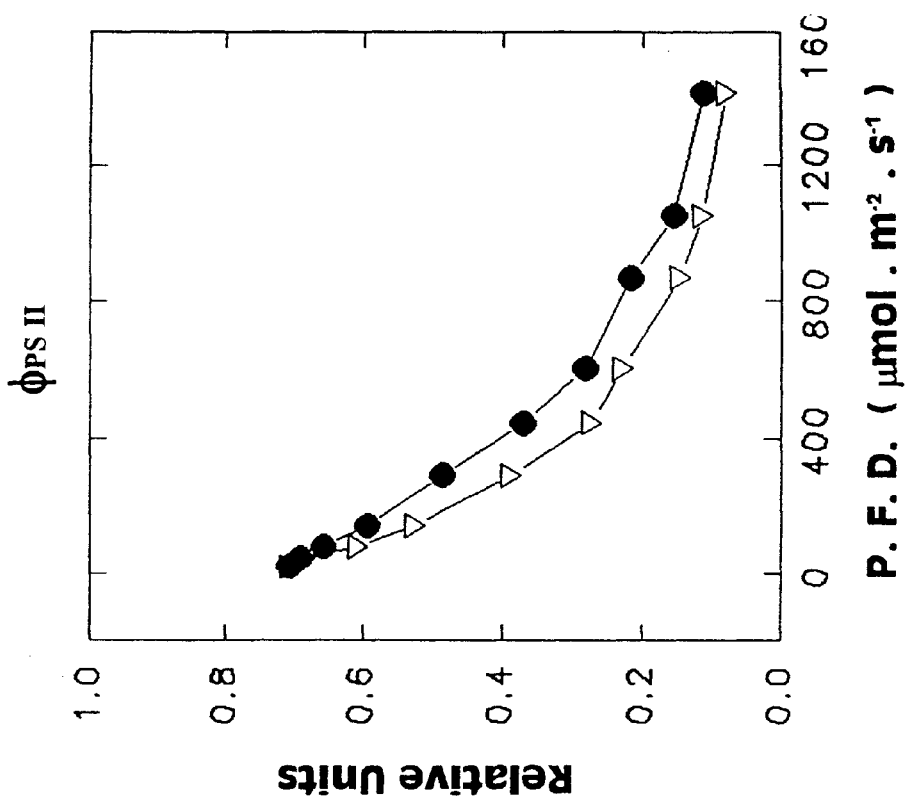
Figure 13C:
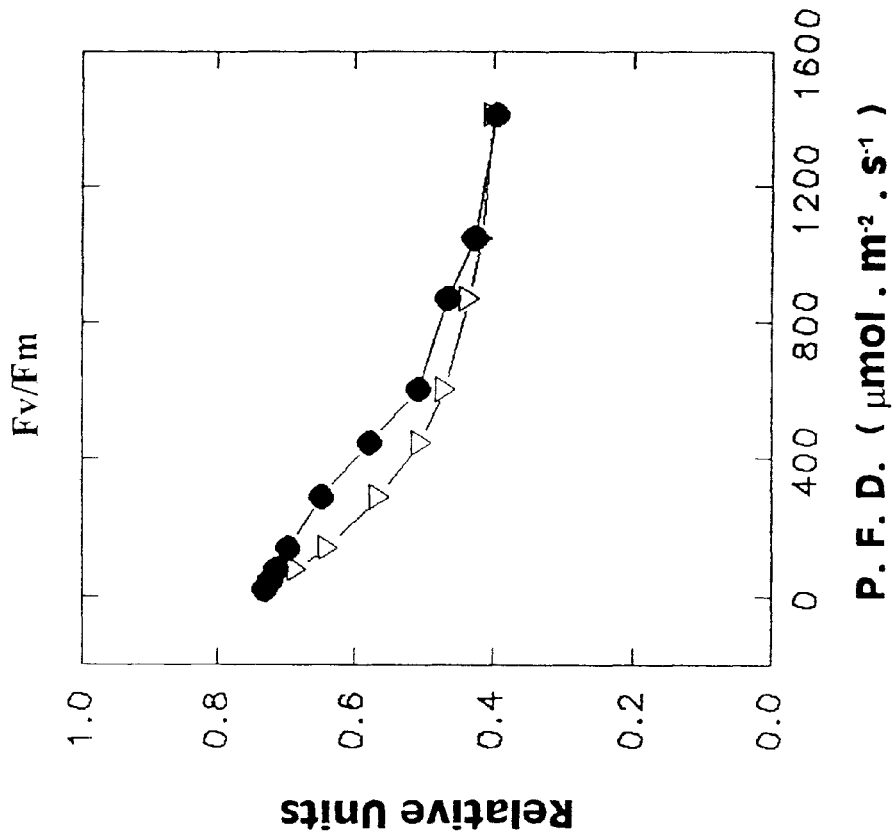

Non-photochemical quenching (qN) was higher in WT from 100 to 600 $\mu mol \cdot m^{-2} \cdot s^{-1}$ (FIG. 13B). It is evident that in TR the regulation of PSII function was affected by the enhanced light-absorbing capacity. The higher efficiency flow of low light electron transport by PSII in TR appears to be attributable mainly to a higher Fv/Fm and a lower qN. Conversely, photochemical quenching (qP) becomes the main factor determining the higher efficiency of PSII ($\emptyset_{PSII}$) in TR under light intensities higher than 600 $\mu mol \cdot m^{-2} \cdot s^{-1}$.

These data show that elevating type I LhcIIb Cab protein levels by genetic manipulation results in measurable and significant changes to a plant. LhcII is believed to play a key role in controlling the proportion of absorbed excitation energy directed to PSII. Normally, photosynthesis would be limited in low light by the capacity of electron transport to generate ATP and NADPH for the reduction of $CO_2$; however, the enhanced level of Cab protein allows the TR plants to channel more energy through the electron transport system under light limiting conditions. The presence of elevated LhcIIb Cab proteins could also contribute to changes in reductant and excitation pressures of photosynthesis.

The higher photosynthetic capacity of TR plants is independent of the cultivation lighting parameters. Transgenic plants grown either in low or intermediary irradiance display similar low light photosynthetic capacities, as evident in the higher initial slope of the light response curves exhibited in both saturating and air levels of $CO_2$ (FIGS. 12A–12D and 13A–13D). This suggests higher ATP and NADPH generation capacity as reflected by the metabolite ratio changes at steady state photosynthesis. Lower PGA/TP and higher ATP/ADP ratios in TR plants indicate that elevating Cab protein resulted in increased ATP synthesis, thereby enhancing PGA reduction. The chlorophyll fluorescence parameters also suggest more efficient electron transport in TR plants. The efficiency of excitation energy capture by open PSII centers (the Fv/Fm ratio) was higher in TR plants below 500 $\mu mol \cdot m^{-2} \cdot s^{-1}$ illumination, with a related decrease in non-photochemical quenching (qN) compared to WT plants under the same conditions. The enhanced light-gathering capacity is associated with anatomical modifications to the leaves, e.g., enlargement of intercellular spaces, which probably contribute to increased $CO_2$ diffusion towards the chloroplasts, facilitating higher rates of photosynthetic and carbohydrate synthesis.

All citations in this application to materials and methods are hereby incorporated by reference.

EQUIVALENTS

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A DNA construct comprising:
   a) a promoter;
   b) a 5' untranslated region containing a translational enhancer;
   c) DNA encoding a heterologous plastid-specific transit peptide which enhances protein import;
   d) a gene encoding a nuclear-encoded, plastid membrane protein; and
   e) a 3' untranslated region containing a functional polyadenylation signal.

2. The DNA construct according to claim 1 wherein the construct, incorporated into a plant cell or a cell of a photosynthetic organism, enhances photosynthesis or plastid function of the plant cell or the cell of a photosynthetic organism compared to photosynthesis or plastid function in a wild-type cell under the same growth conditions.

3. The DNA construct according to claim 1, wherein the promoter region is a constitutive promoter.

4. The DNA construct according to claim 3, wherein the constitutive promoter is a 35S cauliflower mosaic virus (CaMV) promoter.

5. The DNA construct according to claim 1, wherein the translational enhancer is a translational enhancer of the 5' untranslated region of the small subunit of ribulose-1,5-bisphosphate carboxylase.

6. The DNA construct according to claim 5, wherein the translational enhancer has a nucleotide sequence comprising residues 1 to 29 of SEQ ID NO:3.

7. The DNA construct according to claim 1, wherein the transit peptide is from the small subunit of ribulose-1,5-bisphosphate carboxylase.

8. The DNA construct according to claim 7, wherein the transit peptide has a nucleotide sequence comprising residues 30 to 215 of SEQ ID NO:3.

9. The DNA construct according to claim 1, wherein the gene encodes a pigment or a pigment-binding protein.

10. The DNA construct according to claim 1, wherein the gene encodes a chlorophyll a/b binding protein.

11. The DNA construct according to claim 1, wherein the gene encodes a chlorophyll a/b binding protein selected from the group consisting of Lhca1, Lhca2, Lhca3, Lhca4, Lhcb1, Lhcb2, Lhcb3, Lhcb4, Lhcb5 and Lhcb6.

12. The DNA construct according to claim 10, wherein the gene encoding a chlorophyll a/b binding protein is a pea cab gene.

13. The DNA construct according to claim 7, wherein the 3' untranslated region comprising a functional polyadenylation signal is from a cab gene.

14. A transgenic plant or photosynthetic organism containing a DNA construct comprising:
   a) a promoter;
   b) a 5' untranslated region containing a translational enhancer;
   c) DNA encoding a heterologous plastid-specific transit peptide which enhances protein import;
   d) a gene encoding a nuclear-encoded, plastid membrane protein; and
   e) a 3' untranslated region containing a functional polyadenylation signal.

15. Seed of the transgenic plant according to claim 14.

16. A plant part derived from the transgenic plant according to claim 14, wherein the plant part contains the DNA construct.

17. The plant part of claim 16 selected from the group consisting of leaves, stems, roots, flowers, tissues, epicotyls, meristems, hypocotyls, cotyledons, pollen, ovaries, cells, and protoplasts.

18. Progeny of the plant or photosynthetic organism according to claim 14 wherein the progeny contains the DNA construct.

19. The progeny according to claim 18 wherein the gene encodes a pigment or a pigment-binding protein.

20. The transgenic plant according to claim 14 wherein the plant is a monocot.

21. The transgenic plant according to claim 14 wherein the plant is a dicot.

22. A transgenic plant or photosynthetic organism according to claim 14 wherein the plant or photosynthetic organism further comprises an additional exogenous nucleic acid sequence.

23. A transgenic plant or photosynthetic organism containing a DNA construct comprising:
    a) a promoter;
    b) a 5' untranslated region comprising the 5' untranslated region of the small submit of ribulose-1,5-bisphosphate carboxylase;
    c) DNA encoding a heterologous transit peptide which has a nucleotide sequence comprising residues 30–215 of SEQ ID NO:3;
    d) a gene encoding a nuclear-encoded pigment-binding membrane protein; and
    e) a 3' untranslated region containing a functional polyadenylation signal.

24. Seed of the transgenic plant according to claim 23.

25. A plant part derived from the transgenic plant according to claim 23, wherein the plant part contains the DNA construct.

26. The plant part of claim 25 selected from the group consisting of leaves, stems, roots, flowers, tissues, epicotyls, meristems, hypocotyls, cotyledons, pollen, ovaries, cells, and protoplasts.

27. Progeny of the plant or photosynthetic organism according to claim 23 wherein the progeny contains the DNA construct.

28. The progeny according to claim 27 wherein the gene encodes a chlorophyll a/b binding protein.

29. The transgenic plant according to claim 23 wherein the plant is a monocot.

30. The transgenic plant according to claim 23 wherein the plant is a dicot.

31. A transgenic plant or photosynthetic organism according to claim 23 wherein the plant or photosynthetic organism further comprises an additional exogenous nucleic acid sequence.

32. A cell or tissue culture containing a DNA construct comprising:
    a) a promoter;
    b) a 5' untranslated region containing a translational enhancer;
    c) DNA encoding a heterologous plastid-specific transit peptide which enhances protein import;
    d) a gene encoding a nuclear-encoded, plastid membrane protein; and
    e) a 3' untranslated region containing a functional polyadenylation signal.

33. A plant regenerated from the cell or tissue culture according to claim 32.

34. A cell or tissue culture according to claim 32 containing an additional exogenous nucleic acid sequence.

35. A plant regenerated from the cell or tissue culture according to claim 34.

36. A method for enhancing the photosynthetic or biosynthetic capability of a plant, tissue culture or photosynthetic organism comprising:
    a) preparing a DNA construct comprising a promoter, a 5' untranslated region containing a translational enhancer, DNA encoding a heterologous plastid-specific transit peptide which enhances protein import, a gene encoding a nuclear-encoded plastid membrane protein, and a 3' untranslated region containing a functional polyadenylation signal;
    b) inserting the DNA construct into a cloning vector; and
    c) transforming a plant, tissue culture or photosynthetic organism with the cloning vector.

37. A method for detecting transformation in plants, plant tissue or a photosynthetic organism consisting of:
    a) preparing a DNA construct comprising a promoter, a 5' untranslated region containing a translational enhancer, DNA encoding a heterologous plastid-specific transit peptide which enhances protein import, a gene encoding a nuclear-encoded plastid membrane protein the expression of which is detectable, and a 3' untranslated region containing a functional polyadenylation signal;
    b) inserting the DNA construct into a cloning vector; and
    c) transforming a plant, tissue culture or photosynthetic organism with the cloning vector so that the protein is expressed, wherein expression of the protein is indicative of transformation.

38. The method of claim 37 wherein the protein is a pigment or pigment-binding molecule.

39. The method of claim 38 wherein the protein is a chlorophyll a/b binding protein.

40. The method according to claim 39 wherein expression, in comparison to wild-type plants under the same conditions, is manifested by one or more of the following characteristics: increased yield, enhanced pigmentation, increased biomass, increased carbohydrate content, more uniform growth, larger seeds or fruits, increased stem girth, enhanced photosynthesis under low light conditions, faster germination, and increased ability to withstand transplant shock.

* * * * *

UNITED STATES PATENT AND TRADEMARK OFFICE
CERTIFICATE OF CORRECTION

Page 1 of 2

PATENT NO. : 6,011,198
DATED : January 4, 2000
INVENTOR(S) : Kenton Ko, et al.

It is certified that error appears in the above-identified patent and that said Letters Patent is hereby corrected as shown below:

Column 2, line 35, replace "(CaNV)" with --(CaMV)--.

Column 13, line 12, replace "*chlamydomonas*" with --*Chlamydomonas*--.

Column 13, lines 65-66, after "Murata." delete paragraph break.

Column 18, line 65, after "for" insert --10--.

Column 25, line 16, after "Following a" insert --30--.

Column 25, line 19, replace "PRBCS-CAB" with --pRBCS-CAB--.

Column 25, line 56, replace "$0.7_{OD}$" with --$0.7_{OD}$--.

Column 27, line 43, after "3 and" insert --5--.

Column 28, line 12, replace "Cab/oeel" with --Cab/Oeel--.

Column 30, line 8, replace "FA" with --$F_A$--.

UNITED STATES PATENT AND TRADEMARK OFFICE
CERTIFICATE OF CORRECTION

PATENT NO. : 6,011,198
DATED : January 4, 2000
INVENTOR(S) : Kenton Ko, Zdenka W. Ko, et al.

It is certified that error appears in the above-identified patent and that said Letters Patent is hereby corrected as shown below:

Claim 23, column 41, line 22, replace "submit" with --subunit--.

Signed and Sealed this

Twenty-sixth Day of December, 2000

Attest:

Q. TODD DICKINSON

Attesting Officer

Director of Patents and Trademarks